(12) United States Patent
Enami et al.

(10) Patent No.: US 10,344,099 B2
(45) Date of Patent: Jul. 9, 2019

(54) ANTIBODY AND ANTIBODY COMPOSITION PRODUCTION METHOD

(71) Applicant: ZENYAKU KOGYO KABUSHIKIKAISHA, Bunkyo-ku (JP)

(72) Inventors: Jumpei Enami, Nerima-ku (JP); Tetsuo Sasaki, Nerima-ku (JP); Hirokazu Suzuki, Nerima-ku (JP)

(73) Assignee: ZENYAKU KOGYO KABUSHIKIKAISHA, Bunkyo-ku (JP)

(*) Notice: Subject to any disclaimer, the term of this patent is extended or adjusted under 35 U.S.C. 154(b) by 0 days.

(21) Appl. No.: 14/439,830

(22) PCT Filed: Nov. 1, 2013

(86) PCT No.: PCT/JP2013/079797
§ 371 (c)(1),
(2) Date: Apr. 30, 2015

(87) PCT Pub. No.: WO2014/069647
PCT Pub. Date: May 8, 2014

(65) Prior Publication Data
US 2015/0291703 A1  Oct. 15, 2015

(30) Foreign Application Priority Data

Nov. 5, 2012 (JP) .................................. 2012-243984

(51) Int. Cl.
| C07K 16/46 | (2006.01) |
| C07K 16/28 | (2006.01) |
| A61K 39/395 | (2006.01) |
| A61K 39/00 | (2006.01) |

(52) U.S. Cl.
CPC ........ *C07K 16/468* (2013.01); *A61K 39/3955* (2013.01); *C07K 16/2878* (2013.01); *C07K 16/2887* (2013.01); *C07K 16/2896* (2013.01); *A61K 2039/507* (2013.01); *C07K 2317/10* (2013.01); *C07K 2317/31* (2013.01); *C07K 2317/52* (2013.01); *C07K 2317/54* (2013.01); *C07K 2317/55* (2013.01); *C07K 2317/92* (2013.01)

(58) Field of Classification Search
CPC .......... C07K 16/00-468; C07K 16/468; C07K 2317/10; C07K 2317/15
See application file for complete search history.

(56) References Cited

U.S. PATENT DOCUMENTS

| 5,747,654 | A | 5/1998 | Pastan et al. |
| 7,183,076 | B2 | 2/2007 | Arathoon et al. |
| 9,527,927 | B2 * | 12/2016 | Chowdhury ......... C07K 16/468 |
| 2005/0106722 | A1 | 5/2005 | Jones et al. |
| 2006/0269989 | A1 | 11/2006 | Miyazaki et al. |
| 2009/0162360 | A1 | 6/2009 | Klein et al. |
| 2009/0232811 | A1 | 9/2009 | Klein et al. |
| 2010/0015133 | A1 | 1/2010 | Igawa et al. |
| 2014/0348839 | A1 | 11/2014 | Chowdhury et al. |

FOREIGN PATENT DOCUMENTS

| CN | 102639561 A | 8/2012 |
| JP | 9 502862 | 3/1997 |
| JP | 2006 515503 | 6/2006 |
| JP | 2011 505848 | 3/2011 |
| JP | 2011 506509 | 3/2011 |
| JP | 2015 502409 | 1/2015 |
| WO | 94 29350 | 12/1994 |
| WO | 98 50431 | 11/1998 |
| WO | 2004 009618 | 1/2004 |
| WO | 2004 111233 | 12/2004 |
| WO | 2006 106905 | 10/2006 |
| WO | 2007 147901 | 12/2007 |
| WO | 2009 080251 | 7/2009 |
| WO | 2009 080253 | 7/2009 |
| WO | 2009 089004 | 7/2009 |
| WO | 2010 151792 | 12/2010 |
| WO | 2011 034605 | 3/2011 |
| WO | WO 2011/061492 A2 | 5/2011 |
| WO | 2012 025530 | 3/2012 |

OTHER PUBLICATIONS

Schmiedl, et al., "Expression of a bispecific dsFv-dsFv' antibody fragment in *Escherichia coli*", Protein Engineering, vol. 13, No. 10, (2000), pp. 725-734.
International Search Report dated Feb. 4, 2014 in PCT/JP13/079797 Filed Nov. 1, 2013.
Extended European Search Report dated Jun. 22, 2016 in Patent Application No. 13850520.1.
Tuija Teerinen, et al., "Structure-based Stability Engineering of the Mouse IgG1Fab Fragment by Modifying Constant Domains" Journal of Molecular Biology, ScienceDirect, vol. 361, No. 4, XP024951313, Aug. 25, 2006, pp. 687-697.

\* cited by examiner

*Primary Examiner* — Jessica H Roark
(74) *Attorney, Agent, or Firm* — Oblon, McClelland, Maier & Neustadt, L.L.P.

(57) ABSTRACT

[Problem] To provide: an antibody comprising at least two kinds of Fab, and in particular having restricted light chain-heavy chain combinations; a corresponding antibody composition; and production methods for same. [Solution] The present invention provides production methods for (1) an antibody or (2) an antibody composition, the methods using non-natural disulfide bonds.

19 Claims, 22 Drawing Sheets

Specification includes a Sequence Listing.

[Fig. 1]
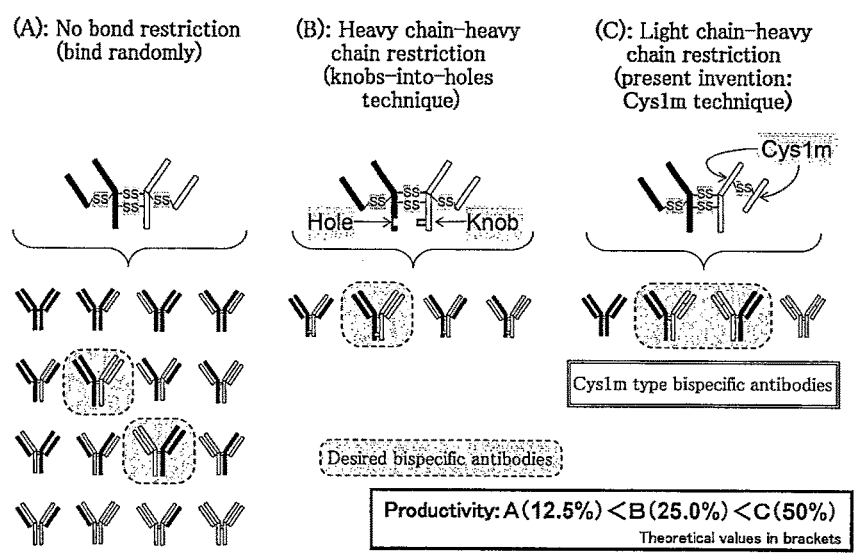

[Fig. 2]

```
P01: TTTCGTACGGTGGCTGCACCATCTGTC
P02: TTTTCTAGATCAACACTCTCCCCTGTTGAAGCT
P03: TTTAAGCTTGGTCAGCCCAAGGC
P04: CGACTCTAGACTATGAACATTCTGT
P05: AAACGTACGGTGGCCAACCCCACTGTCACT
P06: TTTGCTAGCACCAAGGGCCCATCGGTCTT
P07: AAACTCGAGTCATTTACCCGGAGACAGGGA
P08: TCAACAGGGGAGAG TCC TGATCTAGAGTCG
P09: CGACTCTAGATCA GGA CTCTCCCCTGTTGA
P10: AAACGTACGGTGGCTGCACCATCTGTC TGC ATCTTCCCGCCATC
P11: CATCTGTCTTCATC TGC CCGCCATCTGATG
P12: CATCAGATGGCGG GCA GATGAAGACAGATG
P13: TTCATCTTCCCGCCA TGC GATGAGCAGTTG
P14: CAACTGCTCATC GCA TGGCGGGAAGATGAA
P15: GATGAG TGC TTGAAATCTGGAACTGCC
P16: TTTCAA GCA CTCATCAGATGGCGGGAA
P17: CTCCCAGGAG TGC GTCACAGAGCAGGACAG
P18: CTGTCCTGCTCTGTGAC GCA CTCCTGGGAG
P19: AATTAACCCTCACTAAAGGG
P20: GTGCCACCTGACGTCTAGAT
P21: CCCTCTAGACTATGA GGA TTCTGTAGGGGCCA
P22: AAACGTACGGTGGCCAACCCCACTGTCACTCTG TGC CCGCCCTCCTCTGAG
P23: CCTCTGAG TGC CTCCAAGCCAACAAGGCCA
P24: TGGAG GCA CTCAGAGGAGGGCGGGAACAGA
P25: GGAGACC TGC AAACCCTCCAAACAGAGCAA
P26: GGAGGGTTT GCA GGTCTCCACTCCCGCCTT
P27: GTTGAGCCCAAATCT TCC GACAAAACTCAC
P28: GTGAGTTTTGTC GGA AGATTTGGGCTCAAC
P29: TCAGCTAGCACCAAGGGCCCATCGGTC TGC CCCTGGCACCCTC
P30: CCCATCGGTCTTC TGC CTGGCACCCTCCTC
P31: GAGGAGGGTGCCAG GCA GAAGACCGATGGG
P32: CATCGGTCTTCCCC TGC GCACCCTCCTCCA
P33: TGGAGGAGGGTGC GCA GGGGAAGACCGATG
P34: TCCAAG TGC ACCTCTGGGGGCACAGCG
P35: AGAGGT GCA CTTGGAGGAGGGTGCCAG
P36: ACAGCG TGC CTGGGCTGCCTGGTCAAG
P37: GCCCAG GCA CGCTGTGCCCCCAGAGGT
P38: GCGTGCACACC TGC CCGGCTGTCCTAC
P39: GTAGGACAGCCGG GCA GGTGTGCACGC
P40: CGTGCACACCTTC TGC GCTGTCCTACAG
P41: CTGTAGGACAGC GCA GAAGGTGTGCACG
P42: CCGGCT TGC CTACAGTCCTCAGGACTC
P43: CTGTAG GCA AGCCGGGAAGGTGTGCAC
P44: TGCTCCTCCCGCGGCTTTGTCTTGGC
P45: GGCTCTGCACAAC CGCTTC ACGCAGAAGAG
P46: CTCTTCTGCGT GAAGCG GTTGTGCAGAGCC
P47: TAATACGACTCACTATAGGG
```

[Fig. 3]

N01: CGTACGgtggctgcaccatctgtc`ttc`atc`ttc`ccgcca`tct`gatgag`cag`ttgaaatct
ggaactgcctctgttgtgtgcctgctgaataacttctatcccagagaggccaaagtacag
tggaaggtggataacgccctccaatcgggtaactcccaggag`agt`gtcacagagcaggac
agcaaggacagcacctacagcctcagcagcaccctgacgctgagcaaagcagactacgag
aaacacaaagtctacgcctgcgaagtcacccatcagggcctgagctcgcccgtcacaaag
agcttcaacaggggagag`tgt`tgaTCTAGA N02: CGTACGgtggccaaccccactgtcactctg`ttc`ccgccctcctctgag`gag`ctccaagcc
aacaaggccacactagtgtgtctgatcagtgacttctacccgggagctgtgacagtggcc
tggaaggcagatggcagccccgtcaaggcgggagtggagacc`acc`aaaccctccaaacag
agcaacaacaagtacgcggccagcagctacctgagcctgacgcccgagcagtggaagtcc
cacagaagctacagctgccaggtcacgcatgaagggagcaccgtggagaagacagtggcc
cctacagaa`tgt`tcatagTCTAGA N03: GCTAGCaccaaggggcccatcggtc`ttccccctg`gcaccctcctccaag`agc`acctctggg
ggcacagcg`gcc`ctgggctgcctggtcaaggactacttcccgaaccggtgacggtgtcg
tggaactcaggcgccctgaccagcggcgtgcacacc`ttccg`gct`gtc`ctacagtcctca
ggactctactccctcagcagcgtggtgaccgtgccctccagcagcttgggcacccagacc
tacatctgcaacgtgaatcacaagcccagcaacaccaaggtggacaagaaagttgagccc
aaatct`tgt`gacaaaactcacacatgcccaccgtgcccagcacctgaactcctgggggga
ccgtcagtcttcctcttccccccaaaacccaaggacaccctcatgatctcccggacccct
gaggtcacatgcgtggtggtggacgtgagccacgaagaccctgaggtcaagttcaactgg
tacgtggacggcgtggaggtgcataatgccaagacaaagccgcgggaggagcagtacaac
agcacgtaccgggtggtcagcgtcctcaccgtcctgcaccaggactggctgaatggcaag
gagtacaagtgcaaggtctccaacaaagcccctcccagcccccatcgagaaaaccatctcc
aaagccaaagggcagccccgagaaccacaggtgtacaccctgcccccatcccgggatgag
ctgaccaagaaccaggtcagcctgacctgcctggtcaaaggcttctatcccagcgacatc
gccgtggagtgggagagcaatgggcagccggagaacaactacaagaccacgcctcccgtg
ctggactccgacggctccttcttcctctacagcaagctcaccgtggacaagagcaggtgg
cagcaggggaacgtcttctcatgctccgtgatgcatgaggctctgcacaac`cactac`acg
cagaagagcctctccctgtctccgggtaaatgaCTCGAG

```
N04: N01:ttc  -> tgc,  tgt -> tcc
N05: N01:ttc  -> tgc,  tgt -> tcc
N06: N01:tct  -> tgc,  tgt -> tcc
N07: N01:cag  -> tgc,  tgt -> tcc
N08: N01:agt  -> tgc,  tgt -> tcc
N09: N02:ttc  -> tgc,  tgt -> tcc
N10: N02:gag  -> tgc,  tgt -> tcc
N11: N02:acc  -> tgc,  tgt -> tcc
N12: N03:ttc  -> tgc,  tgt -> tcc
N13: N03:ccc  -> tgc,  tgt -> tcc
N14: N03:ctg  -> tgc,  tgt -> tcc
N15: N03:agc  -> tgc,  tgt -> tcc
N16: N03:gcc  -> tgc,  tgt -> tcc
N17: N03:ttc  -> tgc,  tgt -> tcc
N18: N03:ccg  -> tgc,  tgt -> tcc
N19: N03:gtc  -> tgc,  tgt -> tcc
N20: N03:cactac -> cgcttc
```

[Fig. 4]

A01: RTVAAPSV[F]I[F]P[S]DE[Q]LKSGTASVVCLLNNFYPREAKVQWKVDNALQSGNSQE[S]VTEQD
     SKDSTYSLSSTLTLSKADYEKHKVYACEVTHQGLSSPVTKSFNRGE[C]

A02: RTVANPTVTL[F]PPSSE[E]LQANKATLVCLISDFYPGAVTVAWKADGSPVKAGVET[T]KPSKQ
     SNNKYAASSYLSLTPEQWKSHRSYSCQVTHEGSTVEKTVAPTE[C]S

A03: ASTKGPSV[FPL]APSSK[S]TSGGTA[A]LGCLVKDYFPEPVTVSWNSGALTSGVHT[FP]A[V]LQSS
     GLYSLSSVVTVPSSSLGTQTYICNVNHKPSNTKVDKKVEPKS[C]DKTHTCPPCPAPELLGG
     PSVFLFPPKPKDTLMISRTPEVTCVVVDVSHEDPEVKFNWYVDGVEVHNAKTKPREEQYN
     STYRVVSVLTVLHQDWLNGKEYKCKVSNKALPAPIEKTISKAKGQPREPQVYTLPPSRDE
     LTKNQVSLTCLVKGFYPSDIAVEWESNGQPENNYKTTPPVLDSDGSFFLYSKLTVDKSRW
     QQGNVFSCSVMHEALHN[HY]TQKSLSLSPGK

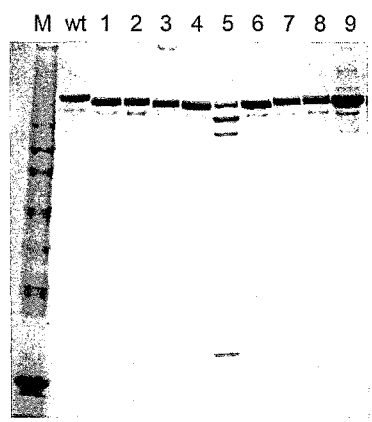

M : molecular weight marker
wt: [anti-CD20 antibody] wild-type light chain, wild-type heavy chain
1: [anti-CD20 antibody] Cys1m (a) = F116C and C214S light chain, S134C and C220S heavy chain
2: [anti-CD20 antibody] Cys1m (b) = F116C and C214S light chain, A141C and C220S heavy chain
3: [anti-CD20 antibody] Cys1m (c) = F118C and C214S light chain, L128C and C220S heavy chain
4: [anti-CD20 antibody] Cys1m (d) = S121C and C214S light chain, F126C and C220S heavy chain
5: [anti-CD20 antibody] Cys1m (e) = S121C and C214S light chain, P127C and C220S heavy chain
6: [anti-CD20 antibody] Cys1m (f) = Q124C and C214S light chain, F126C and C220S heavy chain
7: [anti-CD20 antibody] Cys1m (g) = S162C and C214S light chain, F170C and C220S heavy chain
8: [anti-CD20 antibody] Cys1m (h) = S162C and C214S light chain, P171C and C220S heavy chain
9: [anti-CD20 antibody] Cys1m (i) = S162C and C214S light chain, V173C and C220S heavy chain

[Fig. 6]

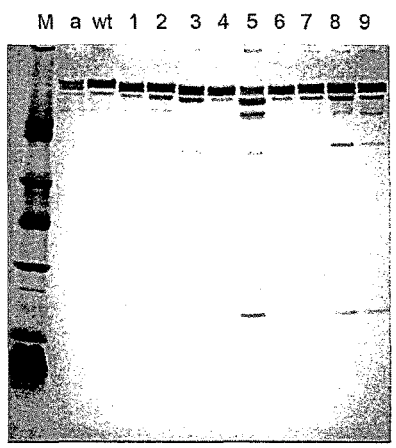

M : molecular weight marker
a: anti-CD20 antibody
wt: [anti-CD37 antibody] wild-type light chain, wild-type heavy chain
1: [anti-CD37 antibody] Cys1m (a) = F116C and C214S light chain, S134C and C220S heavy chain
2: [anti-CD37 antibody] Cys1m (b) = F116C and C214S light chain, A141C and C220S heavy chain
3: [anti-CD37 antibody] Cys1m (c) = F118C and C214S light chain, L128C and C220S heavy chain
4: [anti-CD37 antibody] Cys1m (d) = S121C and C214S light chain, F126C and C220S heavy chain
5: [anti-CD37 antibody] Cys1m (e) = S121C and C214S light chain, P127C and C220S heavy chain
6: [anti-CD37 antibody] Cys1m (f) = Q124C and C214S light chain, F126C and C220S heavy chain
7: [anti-CD37 antibody] Cys1m (g) = S162C and C214S light chain, F170C and C220S heavy chain
8: [anti-CD37 antibody] Cys1m (h) = S162C and C214S light chain, P171C and C220S heavy chain
9: [anti-CD37 antibody] Cys1m (i) = S162C and C214S light chain, V173C and C220S heavy chain

[Fig. 7]

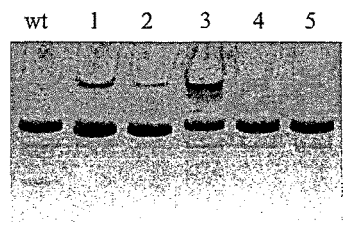

wt: [anti-CD20 antibody] wild-type light chain, wild-type heavy chain
1: [anti-CD20 antibody] Cys1m (j) = F118C and C214S light chain, L128C and C220S heavy chain
2: [anti-CD20 antibody] Cys1m (k) = E124C and C214S light chain, F126C and C220S heavy chain
3: [anti-CD20 antibody] Cys1m (l) = T162C and C214S light chain, F170C and C220S heavy chain
4: [anti-CD20 antibody] Cys1m (m) = T162C and C214S light chain, P171C and C220S heavy chain
5: [anti-CD20 antibody] Cys1m (n) = T162C and C214S light chain, V173C and C220S heavy chain

[Fig. 8]

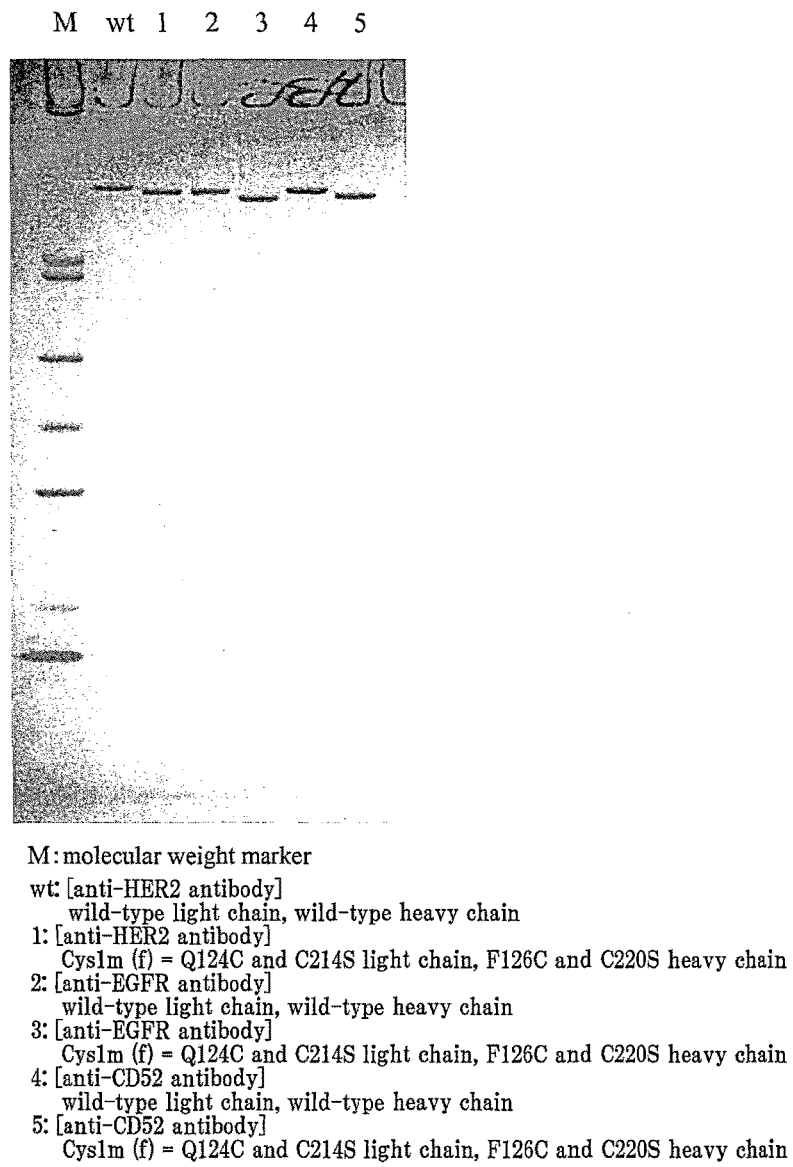

M: molecular weight marker
wt: [anti-HER2 antibody]
    wild-type light chain, wild-type heavy chain
1: [anti-HER2 antibody]
    Cys1m (f) = Q124C and C214S light chain, F126C and C220S heavy chain
2: [anti-EGFR antibody]
    wild-type light chain, wild-type heavy chain
3: [anti-EGFR antibody]
    Cys1m (f) = Q124C and C214S light chain, F126C and C220S heavy chain
4: [anti-CD52 antibody]
    wild-type light chain, wild-type heavy chain
5: [anti-CD52 antibody]
    Cys1m (f) = Q124C and C214S light chain, F126C and C220S heavy chain

[Fig. 9]
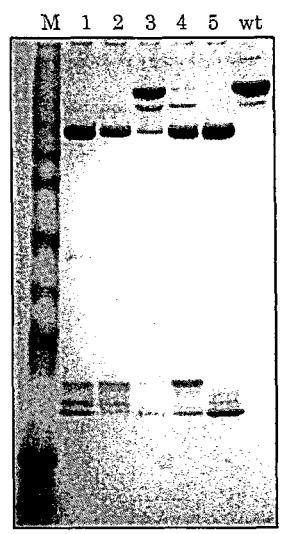
M : molecular weight marker
1: F116C and C214S light chain, wild-type heavy chain
2: F118C and C214S light chain, wild-type heavy chain
3: S121C and C214S light chain, wild-type heavy chain
4: Q124C and C214S light chain, wild-type heavy chain
5: S162C and C214S light chain, wild-type heavy chain
wt: wild-type light chain, wild-type heavy chain

[Fig. 10]

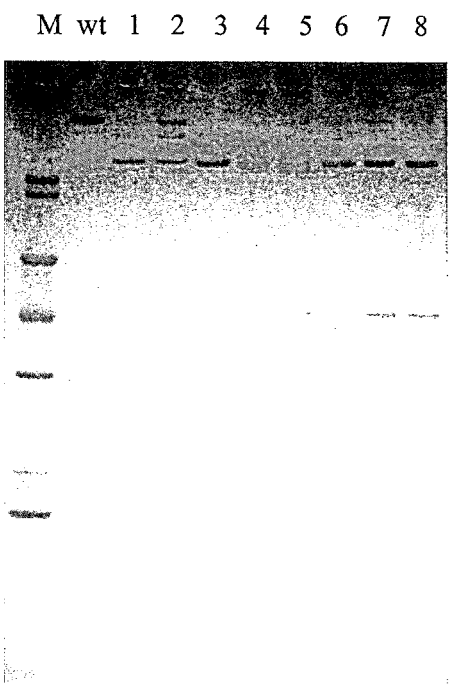

M: molecular weight marker
wt: wild-type light chain, wild-type heavy chain
1: F118C and C214S light chain, wild-type heavy chain
2: E124C and C214S light chain, wild-type heavy chain
3: T162C and C214S light chain, wild-type heavy chain
4: wild-type light chain, L128C and C220S heavy chain
5: wild-type light chain, F126C and C220S heavy chain
6: wild-type light chain, F170C and C220S heavy chain
7: wild-type light chain, P171C and C220S heavy chain
8: wild-type light chain, V173C and C220S heavy chain

[Fig. 11]

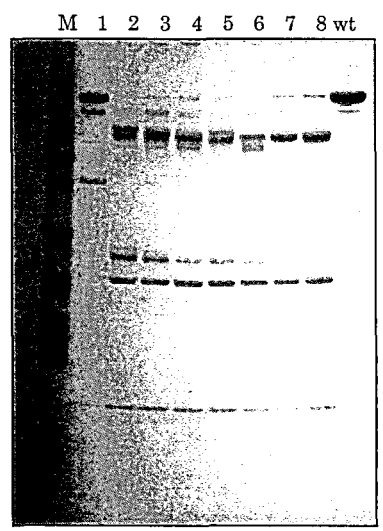

M : molecular weight marker
1: wild-type light chain, S134C and C220S heavy chain
2: wild-type light chain, A141C and C220S heavy chain
3: wild-type light chain, L128C and C220S heavy chain
4: wild-type light chain, F126C and C220S heavy chain
5: wild-type light chain, F170C and C220S heavy chain
6: wild-type light chain, P127C and C220S heavy chain
7: wild-type light chain, P171C and C220S heavy chain
8: wild-type light chain, V173C and C220S heavy chain
wt: wild-type light chain, wild-type heavy chain

[Fig.12]
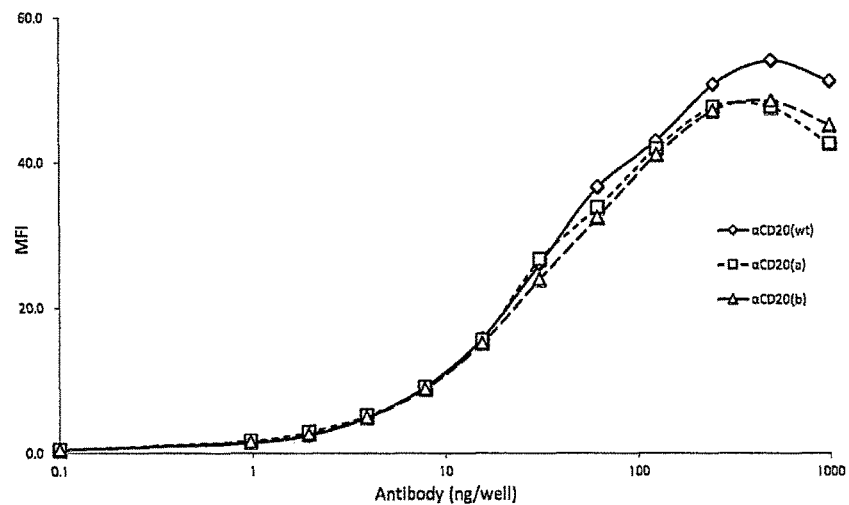
[Fig.13]
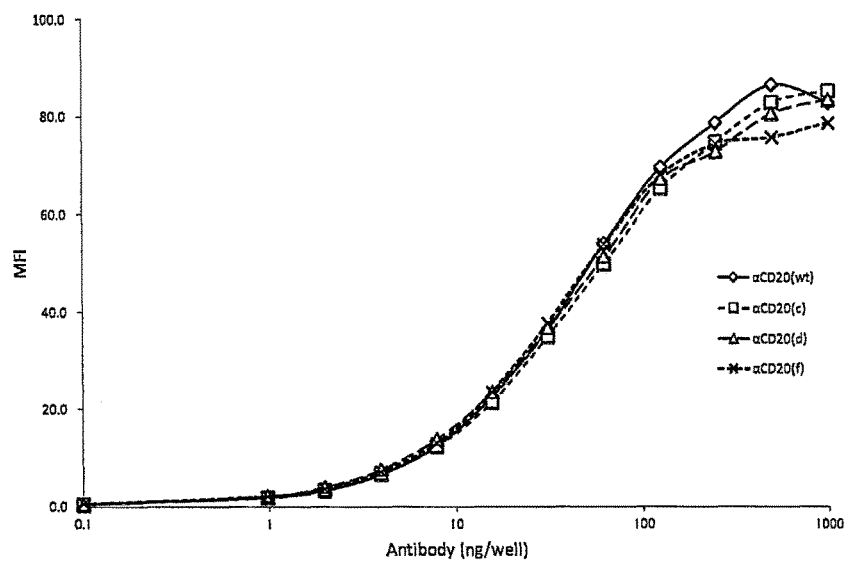

[Fig.14]
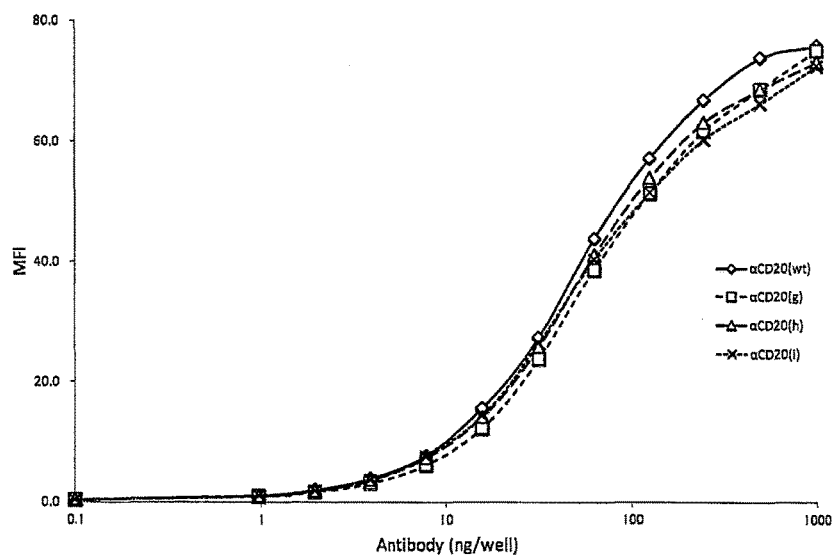
[Fig.15]
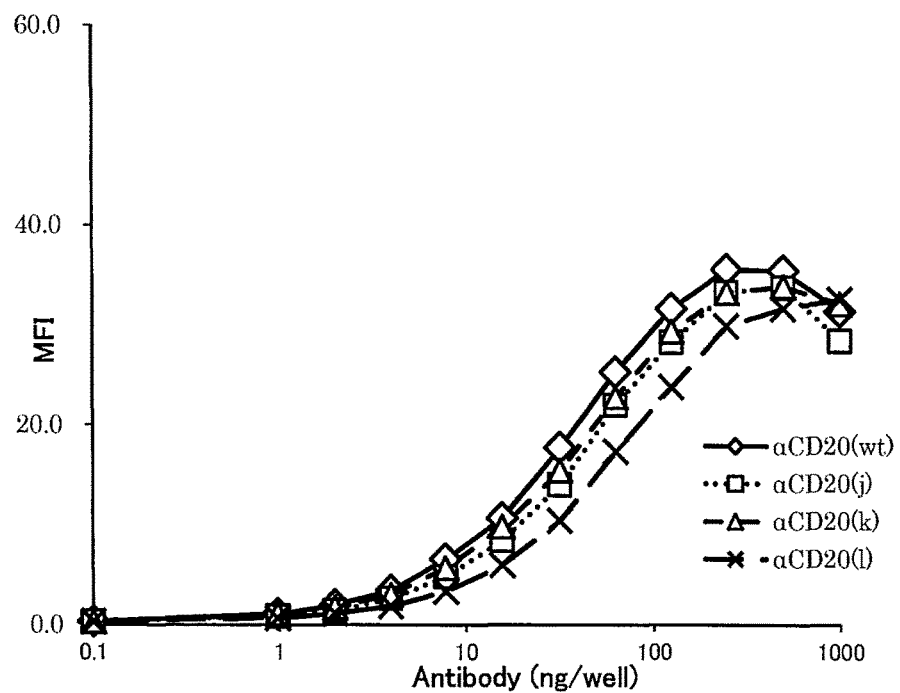

[Fig.16]
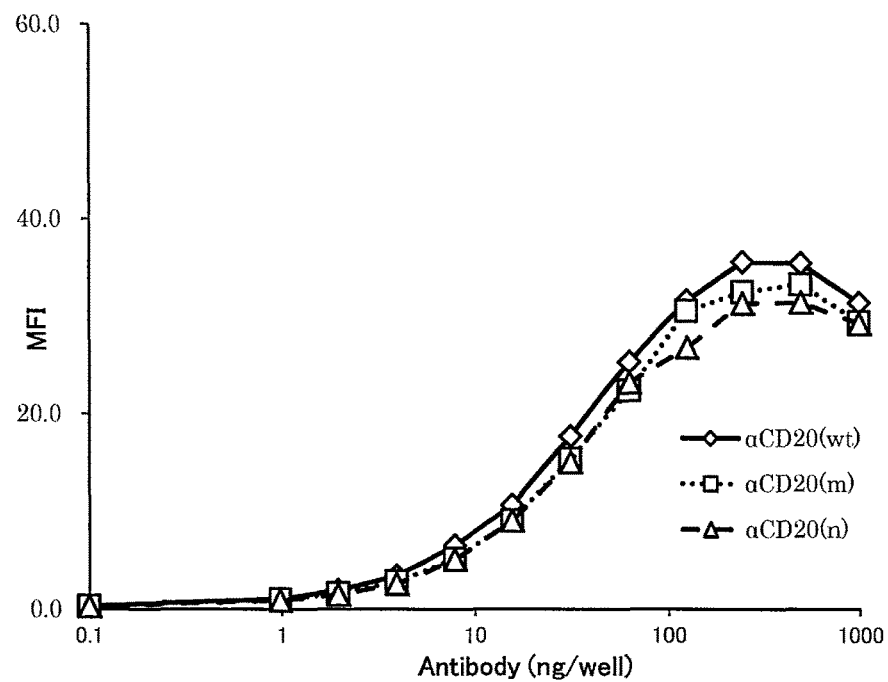
[Fig.17]
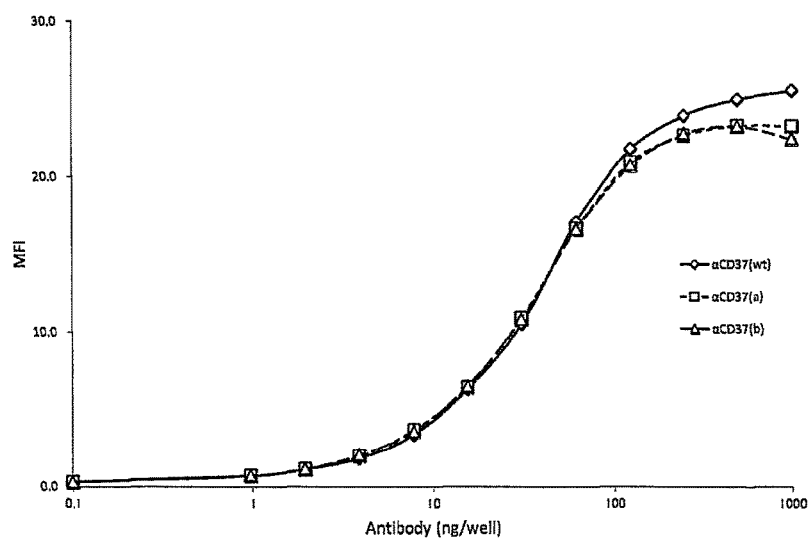

[Fig.18]
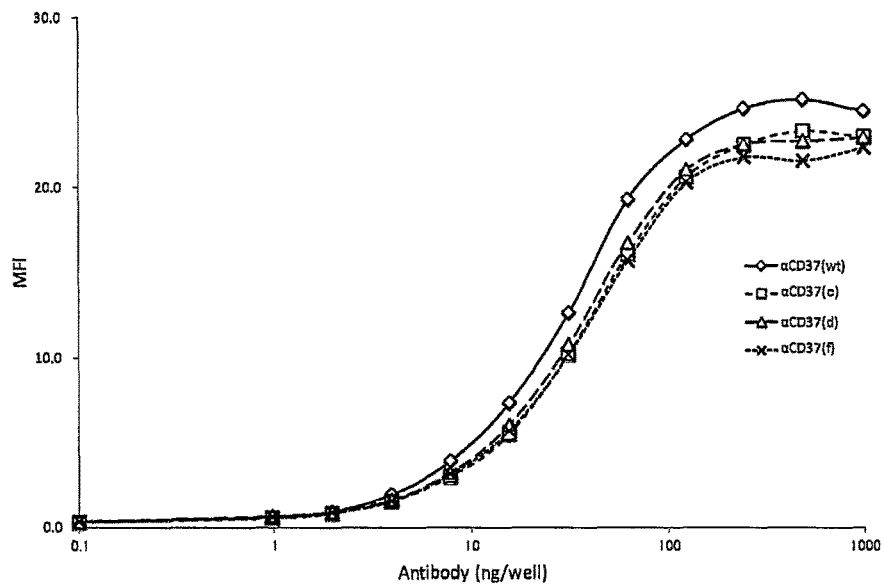
[Fig.19]
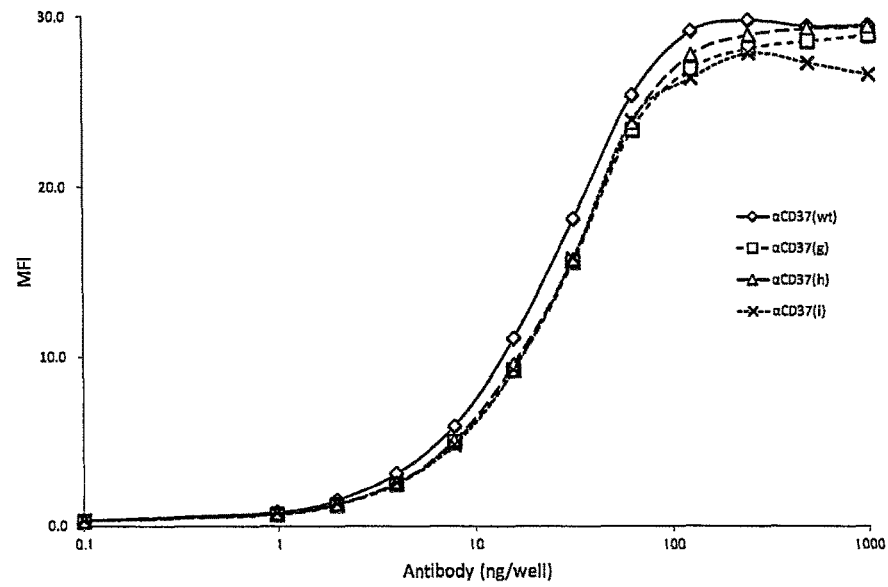

[Fig.20]
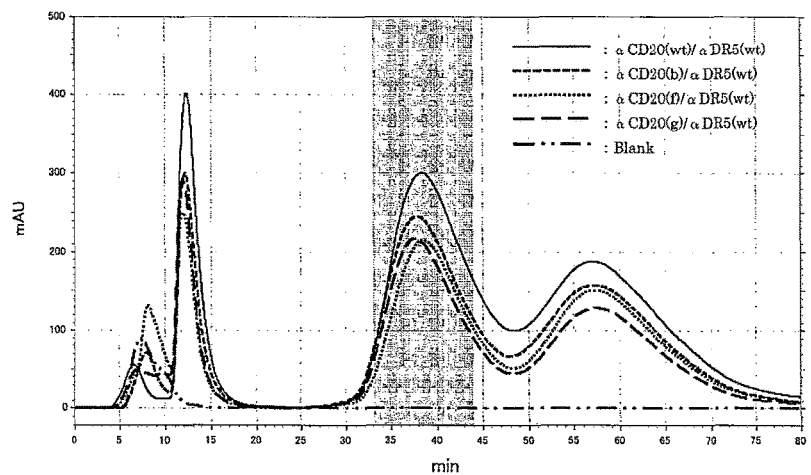
[Fig.21]
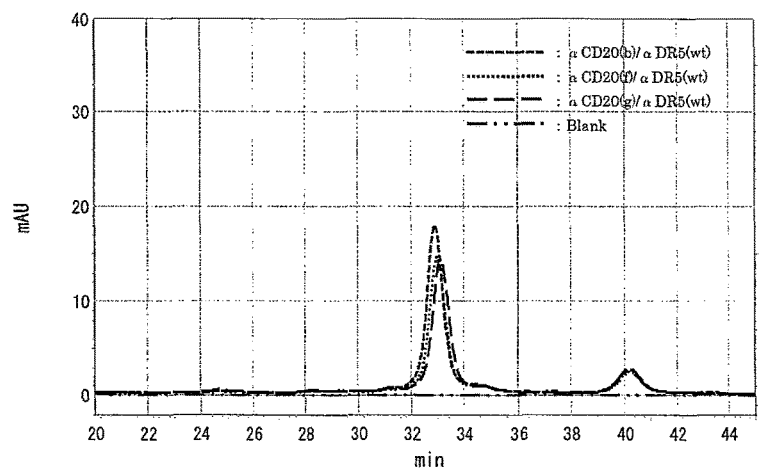
[Fig.22]
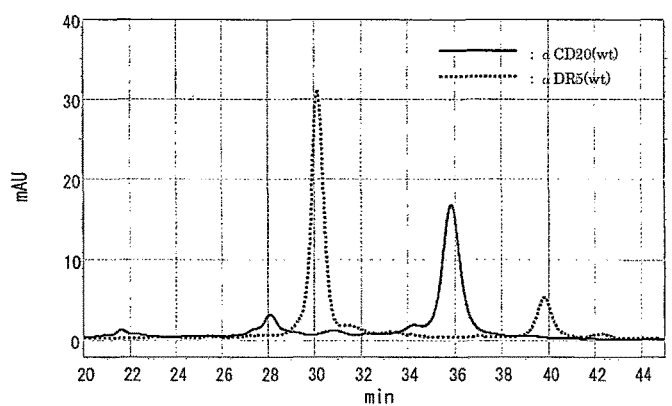

[Fig.23]
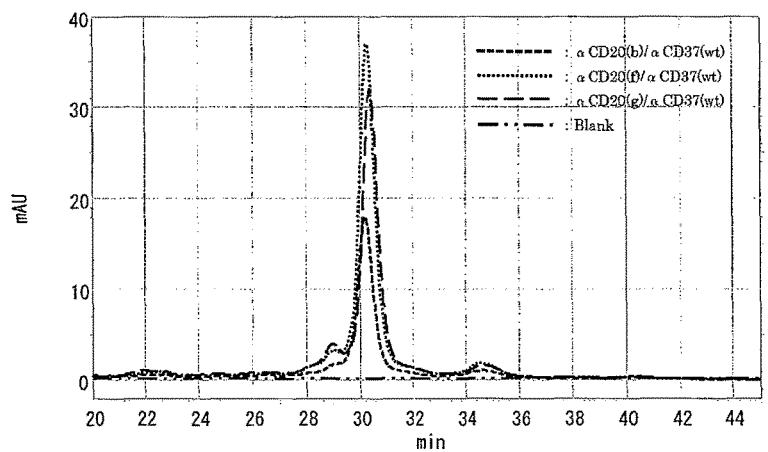
[Fig.24]
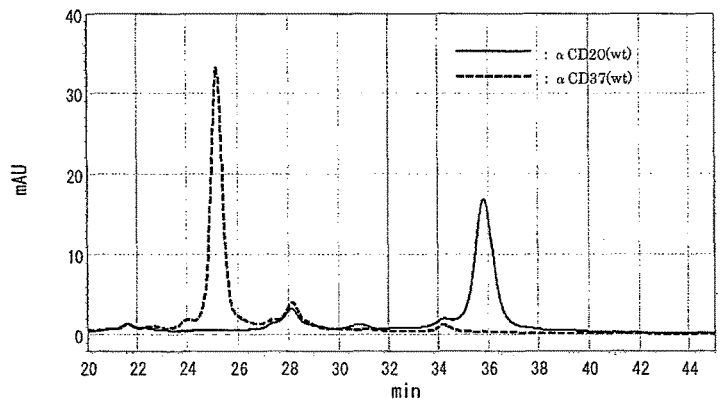
[Fig.25]
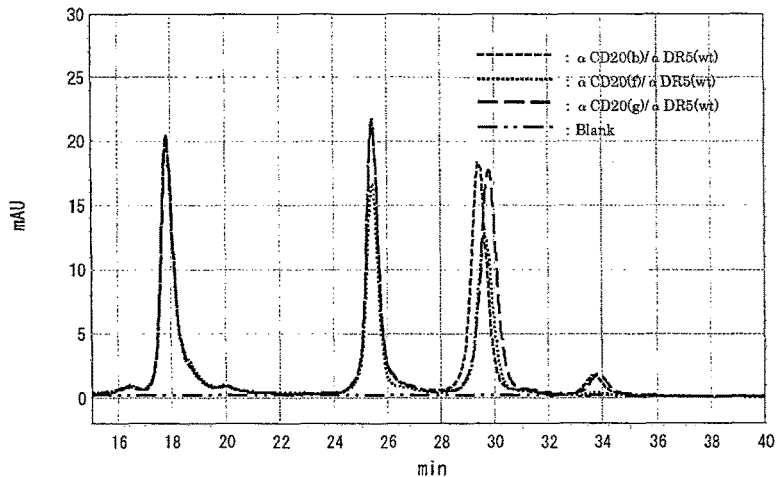

[Fig.26]
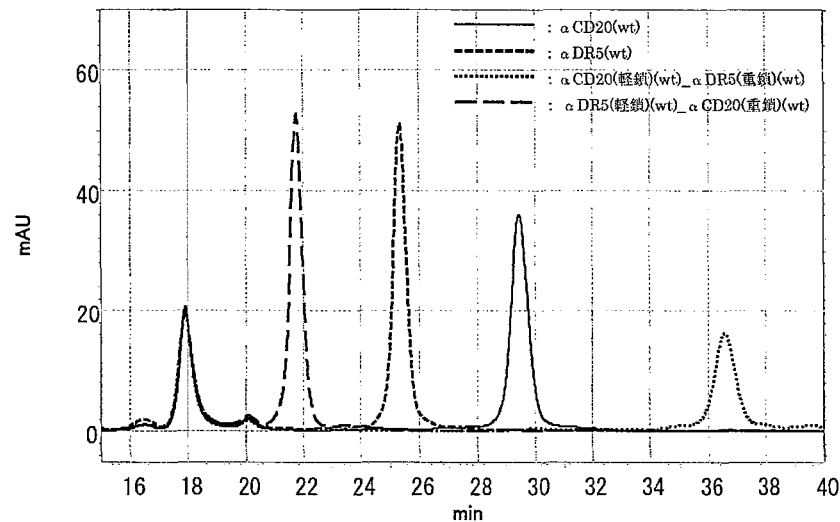
[Fig.27]
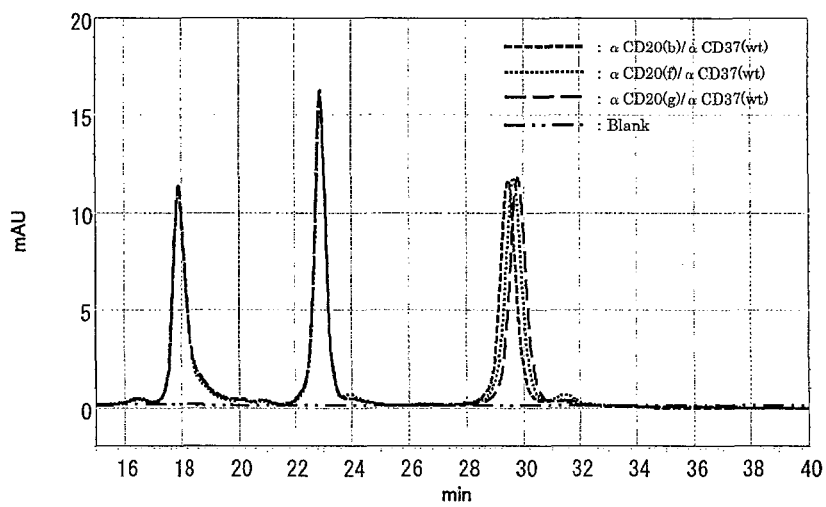

[Fig.28]
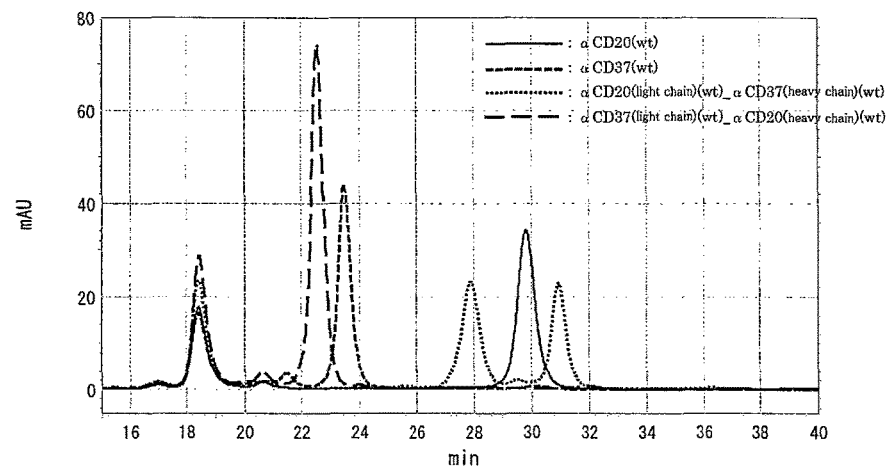
[Fig.29]
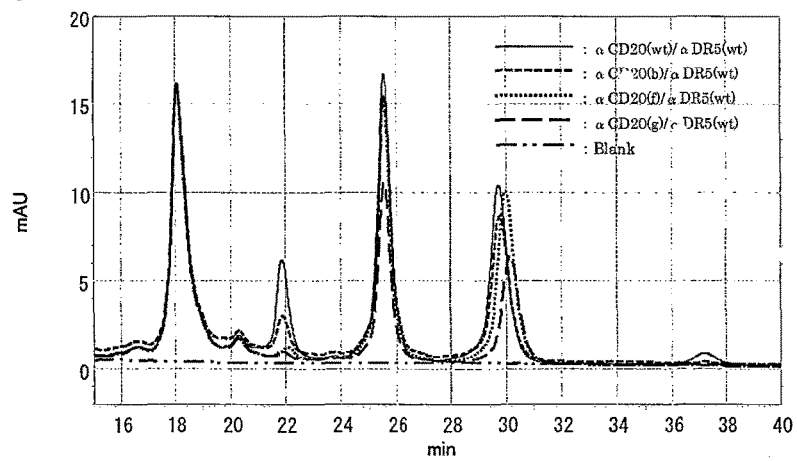

[Fig.30]
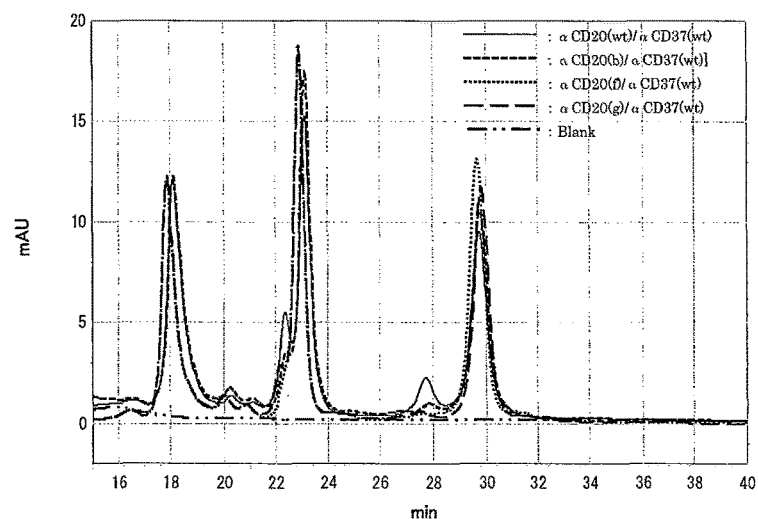
[Fig.31]
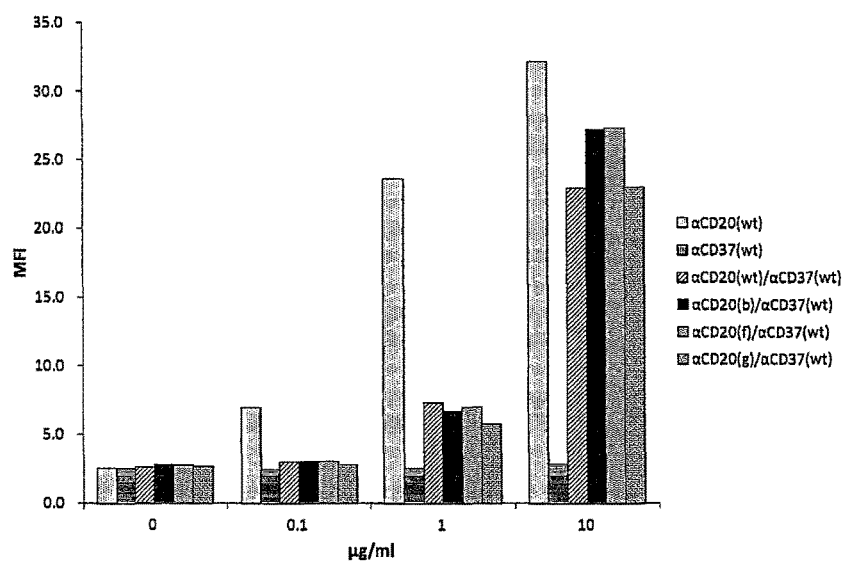

[Fig.32]
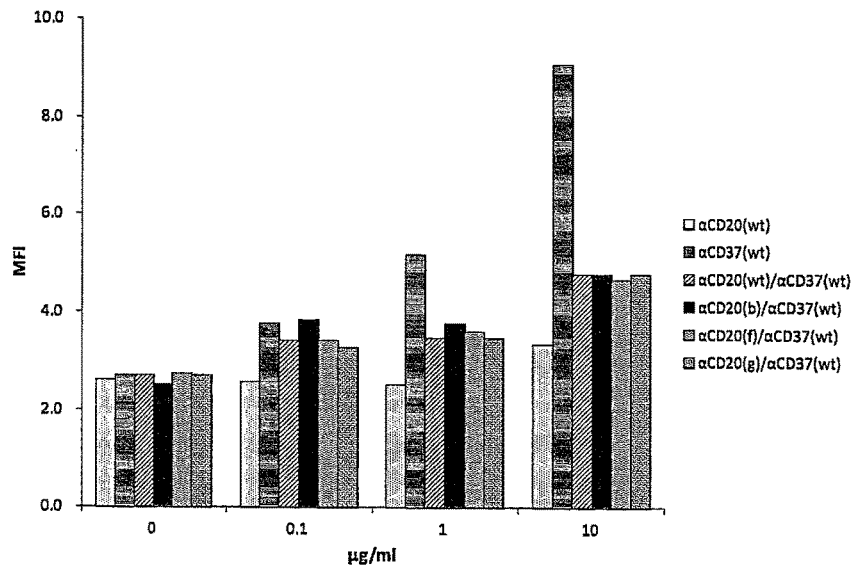
[Fig.33]
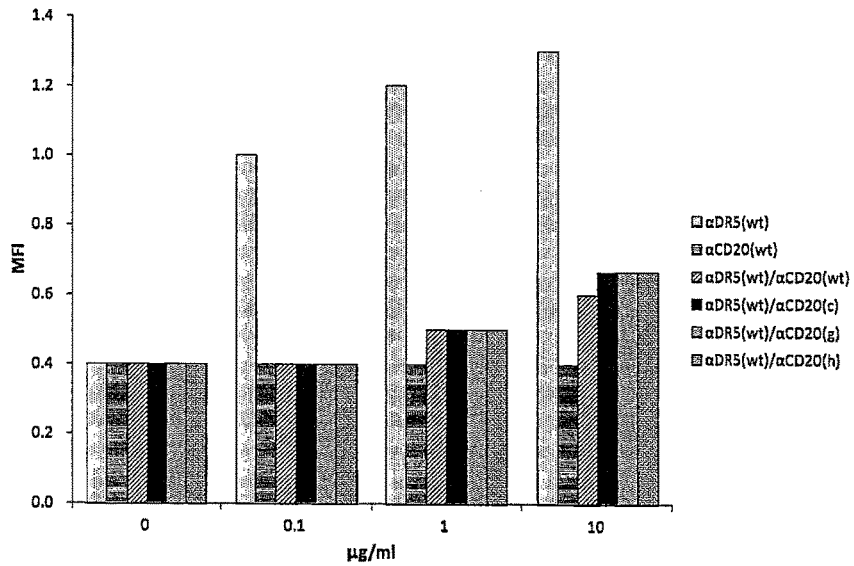

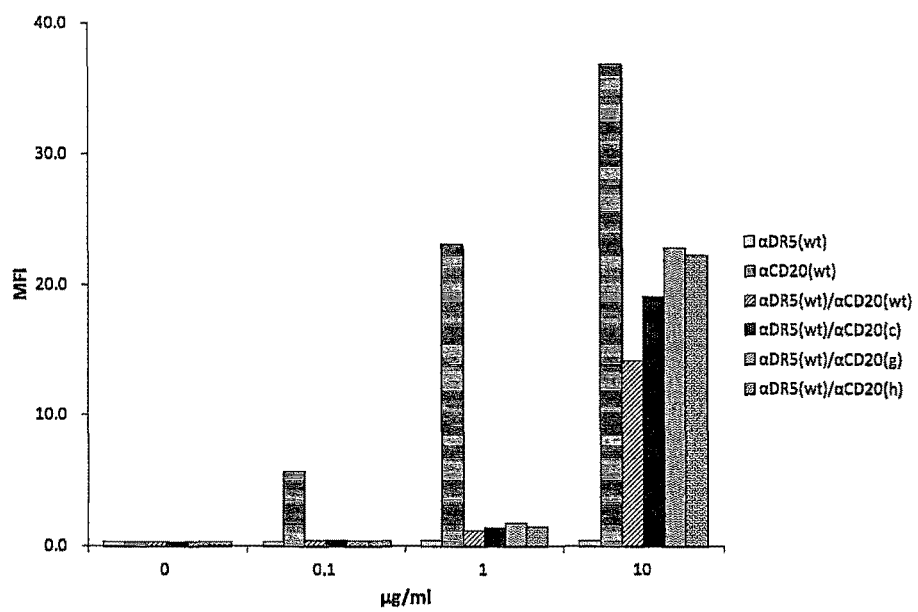
[Fig.34]

ANTIBODY AND ANTIBODY COMPOSITION PRODUCTION METHOD

TECHNICAL FIELD

The present invention relates to an antibody comprising at least two different Fab regions, in particular an antibody with a restricted light chain-heavy chain combination, a corresponding antibody composition or a production method thereof.

BACKGROUND ART

Due to the specific property of allowing simultaneous binding to at least two different antigens, multispecific antibodies, such as bispecific antibodies with two different antigen-recognition sites, have been expected to be developed as drugs or diagnostic agents. However, that has been impeded by low productivity and difficulties in purification, and there has been little progress towards practicalization.

Moreover, while there are several known methods for effectively producing multispecific antibodies, most attempt to effectively produce multispecific antibodies by restricting heavy chain-heavy chain bonds (Patent Documents 1-6).

Additionally, the disclosures of the following patent documents are all incorporated in the present specification by reference.

Patent Document 1: WO 98/50431
Patent Document 2: WO 2010/151792
Patent Document 3: U.S. Pat. No. 7,183,076
Patent Document 4: WO 2009/089004
Patent Document 5: WO 2007/147901
Patent Document 6: WO 2011/034605

SUMMARY OF THE INVENTION

The present inventors diligently studied the problems of low productivity and difficulties in purification when producing an antibody comprising two different Fab regions; or a composition wherein the Fab regions are different between at least two antibodies, and found that they can be made effectively by using non-natural disulfide bonds. In other words, according to the present invention, an antibody having a specific combination of heavy chain and light chain can be made efficiently.

The present invention provides a method for making (1) an antibody; or (2) an antibody-containing composition; the method using a non-natural disulfide bond.

The above (1) antibody comprises at least two Fab regions, and at least two of the included Fab regions are different.

Moreover, the above (2) composition comprises at least two kinds of antibodies comprising a Fab region, and of the Fab regions of the included antibodies, at least two are different.

According to this method, the above antibody or composition can be made effectively.

In one embodiment, this method comprises a step of culturing a host cell comprising a nucleic acid encoding an antibody under conditions to express the antibody.

Additionally, in one embodiment, this method comprises a step of recovering the antibody from a host cell culture.

In one embodiment, at least one Fab region comprises a cysteine residue which forms a non-natural disulfide bond between a light chain and a heavy chain.

Moreover, in one embodiment, the position of a disulfide bond between a certain light chain and heavy chain is different from the position of at least one other disulfide bond between a light chain and a heavy chain included in the antibody or composition. Alternatively, a certain Fab region forms a disulfide bond at a position different from at least one other Fab region included in the antibody or composition.

Furthermore, in one embodiment, the above non-natural disulfide bond and the disulfide bond are disulfide bonds between a CL region and a CH1 region.

Additionally, the present invention provides a method for making an antibody comprising a first Fab region and a second Fab region, by using a non-natural disulfide bond.

The light chain and heavy chain constituting the above first Fab region are each different from the light chain and heavy chain constituting the above second Fab region.

According to this method, the above antibody can be made efficiently.

In one embodiment, this method comprises a step of substituting at least one amino acid residue other than cysteine in a CL region and CH1 region of the first Fab region in a parent antibody corresponding to the desired antibody with a cysteine residue which forms or can form a disulfide bond.

Moreover, in one embodiment, this method comprises a step of forming a non-natural disulfide bond in the first Fab region by the cysteine residue which forms or can form a disulfide bond.

Additionally, in one embodiment, a step of allowing the first Fab region to form a disulfide bond at a position different from the second Fab region is included.

Furthermore, the present invention provides an antibody made by the above method.

Moreover, the present invention provides an antibody comprising at least two different Fab regions.

In one embodiment, the at least one Fab region in the above antibody comprises a cysteine residue which forms or can form a non-natural disulfide bond between a CL region and a CH1 region, thereby forming a non-natural disulfide bond.

Additionally, in one embodiment, the position of a disulfide bond between a certain CL region and CH1 region is different from the position of a disulfide bond between at least one other CL region and CH1 region. Alternatively, a certain Fab region forms a disulfide bond at a position different from at least one other Fab region.

Furthermore, in one embodiment, the antibody comprises two different Fab regions.

In addition, the present invention provides a composition made by the above method.

Moreover, the present invention provides a composition comprising at least two antibodies comprising a Fab region. Of the Fab regions of the antibodies in the composition, at least two Fab regions are different.

In one embodiment, at least one Fab region in the above antibodies comprises a cysteine residue which forms or can form a non-natural disulfide bond between a light chain and a heavy chain, thereby forming a non-natural disulfide bond.

Additionally, in one embodiment, the position of a disulfide bond between a light chain and a heavy chain of a certain antibody is different from the position of a disulfide bond between a light chain and a heavy chain of at least one other antibody. Alternatively, a Fab region of a certain antibody forms a disulfide bond at a position different from a Fab region of at least one other antibody.

Furthermore, in one embodiment, the above non-natural disulfide bond and the above disulfide bond are disulfide bonds between a CL region and a CH1 region.

In one embodiment, the antibody is a multispecific antibody. In one embodiment, the antibody is a bispecific antibody.

In one embodiment, the antibody is one wherein at least two antibody fragments are connected through a linker or directly.

In one embodiment, the antibody is an antibody fragment.

In one embodiment, the antibody is a chimeric antibody, a humanized antibody or a human antibody.

In one embodiment, the antibody is an antibody wherein an Fc region is substituted with another molecule.

Furthermore, the present invention provides the above method, antibody or composition wherein the non-natural disulfide bond is formed by a cysteine residue introduced at at least one set of light chain-heavy chain positions selected from a) light chain position 116-heavy chain position 134, b) light chain position 116-heavy chain position 141, c) light chain position 118-heavy chain position 128, d) light chain position 121-heavy chain position 126, e) light chain position 121-heavy chain position 127, f) light chain position 124-heavy chain position 126, g) light chain position 162-heavy chain position 170, h) light chain position 162-heavy chain position 171 and i) light chain position 162-heavy chain position 173.

Moreover, the present invention provides the above method, antibody or composition wherein the non-natural disulfide bond is formed by a cysteine residue introduced at at least one set of light chain-heavy chain positions selected from b) light chain position 116-heavy chain position 141, c) light chain position 118-heavy chain position 128, f) light chain position 124-heavy chain position 126, g) light chain position 162-heavy chain position 170, h) light chain position 162-heavy chain position 171 and i) light chain position 162-heavy chain position 173.

Additionally, the present invention provides the above method, antibody or composition wherein the non-natural disulfide bond is formed by a cysteine residue introduced at at least one set of light chain-heavy chain positions selected from b) light chain position 116-heavy chain position 141, f) light chain position 124-heavy chain position 126 and g) light chain position 162-heavy chain position 170, when the light chain is a κ chain; and h) light chain position 162-heavy chain position 171 and i) light chain position 162-heavy chain position 173, when the light chain is a λ chain.

Furthermore, the present invention provides the above method, antibody or composition wherein the non-natural disulfide bond is formed between at least one set of light chain cysteine-heavy chain cysteine selected from a) F116C-S134C, b) F116C-A141C, c) F118C-L128C, d) S121C-F126C, e) S121C-P127C, f) Q124C-F126C, g) S162C-F170C, h) S162C-P171C, i) S162C-V173C, j) F118C-L128C, k) E124C-F126C, l) T162C-F170C, m) T162C-P171C and n) T162C-V173C.

In one embodiment, the non-natural disulfide bond is formed between at least one light chain cysteine-heavy chain cysteine set selected from b) F116C-A141C, c) F118C-L128C, f) Q124C-F126C, g) S162C-F170C, h) S162C-P171C and i) S162C-V173C.

Moreover, in another embodiment, the non-natural disulfide bond is formed between at least one light chain cysteine-heavy chain cysteine set selected from b) F116C-A141C, f) Q124C-F126C and g) S162C-F170C, when the light chain is a κ chain; and m) T162C-P171C and n) T162C-V173C, when the light chain is a λ chain.

Additionally, the present invention provides the above method, antibody or composition wherein a natural disulfide bond is not formed between a CL region and a CH1 region of at least one Fab region.

Moreover, the present invention provides the above method, antibody or composition wherein the position of a disulfide bond between a CL region and a CH1 region in a certain Fab region is entirely different from the position of a disulfide bond between a CL region and a CH1 region in at least one other Fab region.

Furthermore, the present invention provides the above method wherein the host cell is a eukaryotic cell or *E. coli*.

Additionally, the present invention provides the above method combined with the technique of restricting a heavy chain-heavy chain pairing, or an antibody or composition obtained thereby.

BRIEF DESCRIPTION OF THE DRAWINGS

FIG. 1 is a drawing for explaining the utility of the present invention (Cys1m technique).

FIG. 2 is a list of primer sequences used in the examples.

FIG. 3 is a list of cDNA sequences used in the examples.

FIG. 4 is a list of sequences translated from cDNAs used in the examples.

FIG. 5 is an SDS-PAGE image showing the formation of an SS bond in antibodies (Cys1m antibodies (anti-CD20 antibodies)) of the present invention.

FIG. 6 is an SDS-PAGE image showing the formation of an SS bond in antibodies (Cys1m antibodies (anti-CD37 antibodies)) of the present invention.

FIG. 7 is an SDS-PAGE image showing the formation of an SS bond in antibodies (Cys1m antibodies) of the present invention.

FIG. 8 is an SDS-PAGE image showing the formation of an SS bond in antibodies (Cys1m antibodies; anti-HER2 antibody, anti-EGFR antibody, anti-CD52 antibody) of the present invention.

FIG. 9 is an SDS-PAGE image showing the formation of an SS bond in [Cys1m type light chain-wild type heavy chain] antibodies (light chain is a κ chain).

FIG. 10 is an SDS-PAGE image showing the formation of an SS bond in [Cys1m type light chain-wild type heavy chain] or [wild type light chain-Cys1m type heavy chain] antibodies (light chain is a λ chain).

FIG. 11 is an SDS-PAGE image showing the formation of an SS bond in [wild type light chain-Cys1m type heavy chain Cys1m type] antibodies (light chain is a κ chain).

FIG. 12 is a graph showing the antigen-binding capacities of anti-CD20 antibodies with introduced non-natural disulfide bonds (results of examining antigen-binding capacity against CD20 antigen-expressing Ramos cells).

FIG. 13 is a graph showing the antigen-binding capacities of anti-CD20 antibodies with introduced non-natural disulfide bonds (results of examining antigen-binding capacity against CD20 antigen-expressing Ramos cells).

FIG. 14 is a graph showing the antigen-binding capacities of anti-CD20 antibodies with introduced non-natural disulfide bonds (results of examining antigen-binding capacity against CD20 antigen-expressing Ramos cells).

FIG. 15 is a graph showing the antigen-binding capacities of anti-CD20 antibodies with introduced non-natural disulfide bonds (results of examining antigen-binding capacity against CD20 antigen-expressing Ramos cells).

FIG. 16 is a graph showing the antigen-binding capacities of anti-CD20 antibodies with introduced non-natural disulfide bonds (results of examining antigen-binding capacity against CD20 antigen-expressing Ramos cells).

FIG. 17 is a graph showing the antigen-binding capacities of anti-CD37 antibodies with introduced non-natural disulfide bonds (results of examining antigen-binding capacity against CD37 antigen-expressing Ramos cells).

FIG. 18 is a graph showing the antigen-binding capacities of anti-CD37 antibodies with introduced non-natural disulfide bonds (results of examining antigen-binding capacity against CD37 antigen-expressing Ramos cells).

FIG. 19 is a graph showing the antigen-binding capacities of anti-CD37 antibodies with introduced non-natural disulfide bonds (results of examining antigen-binding capacity against CD37 antigen-expressing Ramos cells).

FIG. 20 is a graph showing the protein A affinity purification results of bispecific antibodies αCD20(Cys1m)/αDR5.

FIG. 21 is a graph showing the F(ab')$_2$ analysis results of purified αCD20(Cys1m)/αDR5.

FIG. 22 is a graph showing the F(ab')$_2$ analysis results of parent antibodies αCD20 and αDR5.

FIG. 23 is a graph showing the F(ab')$_2$ analysis results of purified αCD20(Cys1m)/αCD37.

FIG. 24 is a graph showing the F(ab')$_2$ analysis results of parent antibodies αCD20 and αCD37.

FIG. 25 is a graph showing the Fab analysis results of purified αCD20(Cys1m)/αDR5.

FIG. 26 is a graph showing the Fab analysis results of parent antibodies αCD20, αDR5 and light chain mispairings.

FIG. 27 is a graph showing the Fab analysis results of purified αCD20(Cys1m)/αCD37.

FIG. 28 is a graph showing the Fab analysis results of parent antibodies αCD20, αCD37 and light chain mispairings.

FIG. 29 is a graph showing the Fab analysis results of protein A affinity purified samples for αCD20(Cys1m)/αDR5.

FIG. 30 is a graph showing the Fab analysis results of protein A affinity purified samples for αCD20(Cys1m)/αCD37.

FIG. 31 is a graph showing the results of analyzing the antigen-binding capacities of purified αCD20(Cys1m)/αCD37 against CD20[+]CD37[−] cells.

FIG. 32 is a graph showing the results of analyzing the antigen-binding capacities of purified αCD20(Cys1m)/αCD37 against CD20[−]CD37[+] cells.

FIG. 33 is a graph showing the results of analyzing the antigen-binding capacities of purified αDR5/αCD20(Cys1m) against DR5[+]CD20[−] cells.

FIG. 34 is a graph showing the results of analyzing the antigen-binding capacities of purified αDR5/αCD20(Cys1m) against DR5[−]CD20[+] cells.

MODES FOR CARRYING OUT THE INVENTION

[Description of Terminology and Aspects]

In the present specification, the following terms have the meanings indicated below, and each term refers to the aspects indicated below.

"Antibody" refers to a molecule exhibiting affinity for an antigen by an antigen-antibody reaction, and has a pair or two or more pairs of binding sites (Fv). Antibodies, while not restricted thereto, include, for example, full-length antibodies having a pair or two pairs of polypeptide chains comprising a light chain and a heavy chain, as well as parts (fragments) thereof. Each light chain or heavy chain may comprise a variable region (associated with antigen recognition and binding) and a constant region (associated with localization, complement-dependent cytotoxicity and cell-to-cell interaction). Most common full-length antibodies have two light chain variable (VL) regions, two light chain constant (CL) regions, two heavy chain variable (VH) regions and two heavy chain constant (CH) regions. A variable region comprises complementarity determining regions (CDRs), which are sequences giving an antibody antigen specificity, and framework regions (FRs).

As is clear from the above definitions, the "antibody" in the present specification, unless specifically indicated, includes one wherein two or three or more antibodies (for example, antibody fragments such as Fab regions) are connected through a linker or directly (an antibody comprising multiple antibody fragments). While not restricted thereto, for example, an antibody wherein multiple antibody fragments are connected by a linker may be given as such an antibody.

Antibodies include monoclonal antibodies, polyclonal antibodies, multispecific antibodies (for example, bispecific antibodies) formed from at least two antibodies, antibody fragments having a desired biological activity, antibodies wherein a Fc region has been substituted with another molecule and the like. Moreover, antibodies include chimeric antibodies (for example, humanized antibodies), (complete) human antibodies, multivalent antibodies and modified antibodies.

"Modified antibody", while not restricted thereto, includes those with a missing (shortened) or added (lengthened) amino acid sequence while retaining binding capacity, those with a part of the amino acid sequence substituted, those with a sugar chain fully or partially missing or added, and those with another linker or the like added, as well as combinations thereof.

Additionally, particularly when an antibody comprises a Fc region, the antibody may comprise a sugar chain. Natural antibodies produced by mammalian cells typically comprise a branched oligosaccharide generally N-linked to Asn297 in the CH2 domain of the Fc region (for example, see Wright et al., (1997) *Trends Biotechnol.* 15:26-32). Oligosaccharides may include various carbohydrates, for example, mannose, N-acetyl glucosamine (GlcNAc), galactose, and sialic acid, as well as fucose bound to GlcNAc of the "stem" of a bi-branched oligosaccharide structure.

Moreover, to the extent not compromising the effect of the invention, an antibody may be of any class (for example, IgG, IgA, IgM, IgD, IgE) and any subclass (for example, IgG1, IgG2, IgG3, IgG4).

The variable region comprises a segment called a hypervariable region (HVR) or complementarity determining region (CDR) which changes at the highest frequency in the variable region, and a segment called a framework region (FR) which is relatively highly conserved. The light chain and heavy chain variable regions of a natural antibody each comprise three CDRs and four FR regions. The CDRs of each chain, together with the CDRs of another chain, contribute to the formation of an antigen-binding site of the antibody (for example, see Kabat et al., *Sequences of Proteins of Immunological Interest*, 5th Ed. Public Health Service, National Institutes of Health, Bethesda, Md. (1991)).

"Complementarity determining region" or "CDR" (or "hypervariable region", "HVR" or "HV") refers to a region which is hypervariable and forms a loop in the variable region of an antibody. In general, an antibody comprises three CDRs (CDRL1, CDRL2, CDRL3) in VL and three CDRs (CDRH1, CDRH2, CDRH3) in VH.

As the definition of CDR, any definition may be used to the extent not compromising the effect of the present invention. As the definition of CDR, while not limited thereto, a conventional CDR definition used in the relevant technical field, for example, Kabat, Chothia, AbM or Contact, may be used. The Kabat definition is based on sequence changes, and is most commonly used (for example, see Kabat et al., *Sequences of Proteins of Immunological Interest*, 5th Ed. Public Health Service, National Institutes of Health, Bethesda, Md. (1991)). As for Chothia, determination is made with the locations of structural loops taken into account as well (for example, see Chothia and Lesk, *J. Mol. Biol.* 196: 901-917 (1987)). AbM is an intermediate definition of Kabat and Chothia structural loops, and is used by the AbM antibody modeling software of Oxford Molecular. Contact is based on an analysis of complex crystal structures (for example, see MacCallum et al., *J. Mol. Biol.* 262: 732-745 (1996)). These respective CDR definitions are shown below.

TABLE 1

| Loop | Kabat | Chothia | AbM | contact |
| --- | --- | --- | --- | --- |
| CDRL1 | L24-L34 | L26-L32 | L24-L34 | L30-L36 |
| CDRL2 | L50-L56 | L50-L52 | L50-L56 | L46-L55 |
| CDRL3 | L89-L97 | L91-L96 | L89-L97 | L89-L96 |
| CDRH1 (Kabat numbering) | H31-H35B | H26-H32 . . . 34 | H26-H35B | H30-H35B |
| CDRH1 (Chothia numbering) | H31-H35 | H26-H32 | H26-H35 | H30-H35 |
| CDRH2 | H50-H65 | H53-H55 | H50-H58 | H47-H58 |
| CDRH3 | H90-H102 | H96-H101 | H95-H102 | H93-H101 |

A CDR may comprise at least one "extended CDR" of the following. $V_L$ 24-36 or 24-34 (CDRL1), 46-56 or 50-56 (CDRL2), 89-97 or 89-96 (CDRL3), $V_H$ 26-35 (CDRH1), 50-65 or 49-65 (CDRH2), 93-102, 94-102 or 95-102 (CDRH3)

To number amino acid residues of an antibody, the "Kabat numbering system" (variable region residue numbering based on Kabat or Kabat's amino acid position numbering) may be used (for example, see Kabat et al., *Sequences of Proteins of Immunological Interest*, 5th Ed. Public Health Service, National Institutes of Health, Bethesda, Md. (1991)). Based on this numbering, an amino acid sequence may comprise an additive amino acid corresponding to an insertion in a CDR or FR of a variable region. For example, a heavy chain variable region may comprise an amino acid insertion after heavy chain FR residue 82 (residue 82a, 82b, 82c and so on) and after CDRH2 residue 52 (residue 52a). The Kabat number of a residue may be determined by mutually comparing homologous regions of antibody sequences by the standard Kabat numbering sequence.

Moreover, where specifically indicated, another numbering known to those skilled in the art, such as Chothia numbering, may be used.

"EU numbering" or "EU index" is generally used when referring to an immunoglobulin heavy chain constant region (for example, see the International Immunogenetics Information System website (www.imgt.org); Edelman G. M. et al., The covalent structure of an entire γG immunoglobulin molecule, *Proc. Natl. Acad. Sci. USA*, 1969, 63(1), 78-85; Kabat et al., *Sequences of Proteins of Immunological Interest*, 5$^{th}$ Ed. Public Health Service, National Institutes of Health, Bethesda, Md. (1991)). "Kabat EU numbering" or "Kabat EU index" is numbering that combines the aforementioned Kabat numbering and EU numbering, and is widely used to number human IgG1 or the like. In the present specification, unless specifically indicated, residue numbering based on the Kabat EU numbering system is used to number the amino acid residues of an antibody.

"Fab region" (or "Fab portion") refers to a region corresponding to a fragment with antigen binding capacity, of the two kinds of fragments obtained when cleaving an antibody by papain, and refers to something that comprises both a light chain-derived portion and a heavy chain-derived portion. Typically, a Fab region comprises the variable regions of the light chain and heavy chain (VL and VH regions), and also comprises the constant regions of the light chain (CL) and the first constant region of the heavy chain (CH1). The Fab region is a well-known area in the relevant technical field, and may be determined by a conventional method. For example, it is possible to determine whether or not a desired region is a Fab region by using homology with a known antibody or the like, and it is also possible to simply show it as an assembly of domains. Since the boundaries of a Fab region may change, while not restricted thereto, typically, in human IgG1, IgG2, IgG3, IgG4 and IgM, the Fab region consists of the full-length light chain (κ chain and λ chain), which comprises a light chain variable region (of differing length depending on the antibody clone), and a region that is the heavy chain variable region (of differing length depending on the antibody clone) plus the first constant (CH1) region.

"Two different Fab regions" refers to two Fab regions with one or more differences respectively regarding the primary sequences, side chain modifications or conformations of both the light chain portion and heavy chain portion constituting the Fab regions.

"Linker" means a connecting molecule used when connecting a molecule with another molecule, and various substances are well known in the relevant technical field. Molecules to be connected include polypeptides or low molecular weight compounds, and linkages between antibody fragments or between an antibody fragment and another component may be given as examples. Specific linkers, while not restricted thereto, may include, for example, peptides that are several residues to tens of residues in length such as a GS linker ((GGGGS)3); and low molecular weight compounds such as N-succinimidyl 3-(2-pyridyldithio)propionate (SPDP), succinimidyl 6-3-[2-pyridyldithio]propionamido)hexanoate (LC-SPDP), sulfosuccinimidyl 6-3-[2-pyridyldithio]propionamido)hexanoate (sulfo-LC-SPDP), N-succinimidyl 3-(2-pyridyldithio)butyrate (SPDB), succinimidyloxycarbonyl-α-(2-pyridyldithio)toluene (SMPT), succinimidyl 6-(α-methyl)-[2-pyridyldithio]toluamido)hexanoate (LC-SMPT), sulfosuccinimidyl 6-(α-methyl-[2-pyridyldithio]toluamido) hexanoate (sulfo-LC-SMPT), succinimidyl-4-(p-maleimidophenyl)butyrate (SMPB), sulfosuccinimidyl 4-(p-maleimidophenyl)butyrate (sulfo-SMPB), m-maleimidobenzoyl-N-hydroxysuccinimide ester (MBS), m-maleimidobenzoyl-N-hydroxysulfosuccinimide ester (sulfo-MBS), S-acetylmercaptosuccinic anhydride (SAMSA), dimethyl 3,3-dithiobispropionimidate (DTBP) and 2-iminothiolane. Moreover, a non-covalent bond may be included within a linker or between a linker and a molecule to be connected.

When peptides or the like are "different", the difference, while not restricted thereto, may include a difference in the amino acid sequence, a difference in the added sugar chain, a difference in the chemical modification, a difference in the disulfide bond or the like.

Moreover, in the present invention, a difference in the cysteine residue and/or disulfide bond used for the purpose of the present invention preferably is not included in the above differences (in other words, other than the difference in the cysteine residue and/or disulfide bond, there is preferably at least one difference).

"(Light chain) CL region" refers to a constant region of a light chain, and is a region well known in the relevant technical field. While the CL region may be determined by a conventional method, for example, it is possible to determine whether or not a desired region is a CL region by using homology with a known antibody or the like. Since the boundaries of a CL region may change, while not restricted thereto, the CL region in a human κ chain typically consists of 109-214. Moreover, the CL region in a human λ chain typically consists of 109-213.

"(Heavy chain) CH1 region" refers to the first constant region of a heavy chain, and is a region well known in the relevant technical field. The CH1 region defined here may also comprise a part of a hinge region that follows the CH1 region (hinge region that may be included in a Fab region). While the CH1 region may be determined by a conventional method, for example, it is possible to determine whether a desired region is a CH1 region by using homology with a known antibody or the like. Since the boundaries of a CH1 region may change, while not restricted thereto, typically, in a heavy chain of human IgG1, IgG2, IgG3 or IgG4, the CH1 region as defined here consists of amino acid residue numbers 118-215 and an additive part of a hinge region (for example, amino acid residue numbers 216-224); and in a heavy chain of IgM, the CH1 region as defined here consists of amino acid residue numbers 118-216.

"Fc region" refers to a region corresponding to a fragment which does not have antigen binding capacity of the two fragments obtained when cleaving an antibody by papain. Typically, a Fc region means a C-terminal region of a heavy chain of an antibody which generally comprises a part of a hinge region and consists of the second constant (CH2) region and third constant (CH3) region of the heavy chain. While the boundaries of a Fc region of a heavy chain may change, for example, the heavy chain Fc region of human IgG1 generally consists of from the amino acid residue of Thr225 to the carboxyl terminus of the CH3 region.

Based on the amino acid sequence of a constant region of a heavy chain of an antibody, an antibody can be categorized into different classes (for example, the five classes of IgA, IgD, IgE, IgG and IgM, and further the secondary subclasses of IgG1, IgG2, IgG3, IgG4, IgA1 and IgA2, etc.). Heavy chain constant regions corresponding to the above five classes are respectively called α, δ, ε, γ and μ.

Additionally, the light chains of an antibody may be regarded either as kappa (κ) or lambda (λ) based on its amino acid sequence.

An "effector function" of an antibody means a biological activity of the Fc region of the antibody, and may change depending on the isotype of the antibody. Examples of effector functions of antibodies include C1q affinity, complement-dependent cytotoxicity (CDC), Fc receptor affinity, antibody-dependent cellular cytotoxicity (ADCC), phagocytosis, impairment/blockage of bacterial functions, toxin neutralization and activation of immunocompetent cells (for example, B cells).

The above Fc region is generally the binding site for neutrophils, macrophages, other immune auxiliary cells, complement complexes and receptors in the immune system. This portion may also change, and changes include, for example, an addition or deletion in the amino acid sequence of an antibody, one or more amino acid substitutions and a (sub)class switch.

Furthermore, antibodies also include modified antibodies which have been modified by any well-known method. For example, sugar chain modifications (WO 0061739, etc.) and amino acid mutations in the Fc region (US 20050054832A1) increase binding for Fc receptors, etc. and can provide higher therapeutic effects.

Of "natural antibodies", human IgG is a heterotetrameric glycoprotein which consists of two identical light chains and two identical heavy chains and has a molecular weight of about 150 kDa. Each light chain binds to a heavy chain by one disulfide bond. On the other hand, the heavy chains bind to one another by multiple disulfide bonds, the number of which varies depending on the subclass. In the case of subclass IgG1, there are two disulfide bonds between the heavy chains. Therefore, the total number of disulfide bonds involved in inter-chain bonds is four. Each chain has a variable region on the amino terminal side and a constant region on the carboxyl terminal side. In the middle portion of the heavy chain, i.e., the boundaries of the CH1 region and CH2 region, there is a hinge region which is rich in plasticity, and the heavy chains are bound through two disulfide bonds there. Moreover, the CH3 regions are paired by hydrophobic force. On the other hand, the CL region is paired with the CH1 region by hydrophobic force, and also bound through a disulfide bond. As a result thereof, the VL region and VH region are located in proximity.

"Monoclonal antibody" refers to a group of antibodies that are derived from only one set of antibody genes (one type of light chain and one type of heavy chain), and are substantially uniform at the protein level. Individual antibodies included in the group, except for mutations that may be present at a low level (for example, naturally occurring mutations), are identical. Additionally, monoclonal antibodies may be made according to various conventional methods without adhering to a particular production method. Production methods include, for example, the hybridoma method, recombinant DNA method, phage display technique and the technique of producing a human or human-like antibody in an animal having a gene encoding a human immunoglobulin sequence or the entire or a part of a human immunoglobulin locus.

"Chimeric antibody" refers to an antibody wherein the amino acid sequence of the light chain or heavy chain or both portions is derived from a particular species, and the remaining portion consists of an amino acid sequence derived from another species. Examples include antibodies wherein a variable region derived from an animal antibody such as a rat or mouse antibody is fused to another molecule (for example, a constant region derived from a human antibody).

"Humanized antibody" is a type of chimeric antibody, and is an antibody having a variable region wherein the variable region sequence of the light chain and/or heavy chain has been changed so as to be largely consistent with a known human variable region sequence. Such changes are known in the conventional art, and while not restricted thereto, are typically made by mutation induction or CDR grafting. CDR grafting refers to the grafting of a CDR of an antibody having a desired specificity onto a framework of a human antibody, thereby exchanging the majority of a non-human sequence with a human sequence.

For example, according to the best fit method, a homology search is performed for a variable region sequence of a donor antibody in the entire library of known human variable region sequences, and the human sequence closest to the donor sequence is used as the human framework of the humanized antibody. In another method, a specific framework obtained from the consensus sequences of all human antibodies of a specific light chain or heavy chain subgroup is used. The same framework may be used in several different kinds of humanized antibodies.

An antibody is preferably humanized while maintaining the affinity for an antigen and/or desired biological property. For that reason, for example, a process of using three-dimensional models of a parent antibody sequence and a humanized sequence to analyze the parent antibody sequence and various conceptual humanized products may be performed.

A humanized antibody may comprise a residue not found in the recipient antibody (human antibody) or donor antibody (for example, a mouse antibody). By humanizing a mouse monoclonal antibody, the human anti-mouse antibody (HAMA) response is reduced.

"Human antibody" refers to an antibody wherein the constant regions and variable regions of both the light chain and heavy chain are all derived from human or are substantially identical thereto, and/or an antibody produced using any of the techniques for producing a human antibody disclosed here.

While a human antibody may be made by various conventional techniques, the following methods may be given as examples.

A human antibody may be made by combining a Fv clone variable region sequence selected from a human-derived phage display library with a known human constant region sequence.

Moreover, a human antibody may be prepared by administering an antigen to a transgenic animal capable of producing a complete repertoire of human antibodies in response to an antigen stimulation without producing endogenous immunoglobulins (for example, mouse; for example, immunized XenoMouse) (for example, regarding the XenoMouse technique, see U.S. Pat. Nos. 6,075,181 and 6,150,584). Additionally, homozygous deletion of the antibody heavy chain joining region (JH) gene in germ-line mutant mice is known not to produce endogenous antibodies, and in mice transplanted with embryonic stem cells to which human germ-line immunoglobulin gene sequences have been introduced, human antibodies are produced by antigen administration (for example, see Jakobovits et al., *Proc. Natl. Acad. Sci. USA*, 90: 2551-2555 (1993); Jakobovits et al., *Nature*, 362: 255-258 (1993); Bruggermann et al., *Year in Immunol.*, 7:33-40 (1993)).

Moreover, a human antibody may be made by the human B cell hybridoma technique (for example, see Li et al., *Proc. Natl. Acad. Sci. USA*, 103: 3557-3562 (2006)). Human myeloma or mouse-human hetero-myeloma cell lines for producing human monoclonal antibodies are described in, for example, Kozbor, *J. Immunol.*, 133:3001-3005 (1984); Brodeur et al., *Monoclonal Antibody Production Techniques and Applications*, pp. 51-63 (Marcel Dekker, Inc., New York, 1987); Boerner et al., *J. Immunol.*, 147: 86-95 (1991).

Additionally, in cases where a human antibody has an affinity and property similar to a non-human parent antibody (for example, a mouse antibody), gene shuffling may be used to obtain the human antibody from the non-human parent antibody (also called epitope imprinting; for example, see WO 93/06213). Unlike humanization of a non-human antibody by CDR grafting, a human antibody that does not have any FR or CDR residues of non-human origin can also be obtained by this technique.

"Antibody fragment" refers to a portion of an antibody comprising a sufficient variable region sequence to provide antigen binding. An antibody fragment used as the object of the present invention means a portion of an antibody which comprises a pair or two or more pairs of combinations of a light chain variable region and a heavy chain variable region. Such an antibody portion, while not restricted thereto, includes Fv, Fab and F(ab')$_2$.

These antibody fragments may be made according to a conventional method. For example, they may be made by proteolytic cleavage of an antibody such as pepsin digestion, or a recombination method wherein the light chain and heavy chain cDNAs of an antibody are manipulated to generate light chain and heavy chain fragments. The pepsin treatment of an antibody generates a "F(ab')$_2$" fragment, which has two antigen binding sites and is able to cross-bind to antigens.

Various techniques have been developed to produce antibody fragments. For example, these fragments may be induced by the proteolysis (cleavage, digestion) of antibodies (for example, see Morimoto et al., *Journal of Biochemical and Biophysical Methods* 24: 107-117 (1992); Brennan et al., *Science*, 229: 81-83 (1985)). Moreover, these fragments may also be directly produced by recombinant host cells (for example, *E. coli*). Furthermore, a F(ab')$_2$ fragment may also be formed by chemically linking Fab'-SH fragments recovered from a host cell (for example, see Carter et al., *Bio/Technology* (NY) 10: 163-167 (1992)).

An "Fv" fragment is the smallest antibody fragment comprising a complete antigen binding site. A two-chain Fv generally consists of a dimer of one light chain variable domain and one heavy chain variable domain.

A "Fab" fragment is an antibody fragment that comprises the variable regions of a light chain and a heavy chain (VL and VH regions) and has a light chain constant (CL) region and the first constant (CH1) region of a heavy chain. Additionally, a "F(ab')$_2$" fragment is a pair of Fab' fragments bound by a disulfide bond formed in between by hinge cysteine residues.

"Multivalent antibody" refers to an antibody having three or more antigen binding sites. A multivalent antibody generally has a dimerization domain (for example, a Fc region or a hinge region) and three or more (for example, three to eight, especially four) antigen binding sites (for example, see Tutt et al., *J. Immunol.* 147: 60-69 (1991)).

"Multispecific antibody" refers to an antibody (also including an antibody fragment) having binding specificities for at least two different antigens, and also includes bispecific antibodies.

A bispecific antibody may be made according to a known method. For example, a bispecific antibody may be made by simultaneous expression of two immunoglobulin light chain-heavy chain pairs having different specificities (for example, see Milstein and Cuello, *Nature*, 305:537-539 (1983); WO 93/08829; Traunecker et al., *EMBO J.* 10: 3655-3559 (1991)). In this case, since the light chain and heavy chain are paired randomly, the hybridomas (four hybrids) produce ten different antibody mixtures, one of which has the correct bispecific structure, and is separated/purified by affinity chromatography or the like. Regarding this, methods for more suitably obtaining a bispecific antibody of such a combination are known, and may be used (for example, see WO 94/04690). For more details to produce a bispecific antibody, for example, see Suresh et al., *Methods in Enzymology*, 121: 210-228 (1986).

"Having binding capacity" refers to a molecule (for example, an antibody) having the ability to bind (mainly by non-covalent bonds), particularly the ability to specifically bind, to its binding partner (for example, an antigen).

"Binding affinity" means the overall strength of non-covalent interactions between a single binding site of a molecule (for example, an antibody) and its binding partner (for example, an antigen). Unless particularly indicated, binding affinity means a binding affinity reflecting a 1:1 interaction between the members (for example, an antibody and an antigen) of a binding pair. In general, the affinity of molecule X for its partner Y is expressed as a dissociation constant ($K_d$). Affinity may be measured by a method well known to those skilled in the art. A low affinity antibody tends to bind to an antigen slowly and dissociate quickly, whereas a high affinity antibody stays in the state of binding to an antigen longer.

Antibodies also include antibodies conjugated to one or more drugs (such antibodies are sometimes particularly called "antibody drug conjugates" or "ADC"). Moreover, antibodies also include antibodies conjugated to a peptide, polypeptide or protein. Furthermore, antibodies also include detectably tagged antibodies that are conjugated to one or more tagging markers (radioisotopes or the like). Additionally, an antibody that is not conjugated with a drug, tagging marker or polypeptide, etc. is particularly called a naked antibody.

In such a conjugated antibody, an antibody (Ab) is conjugated to one or more drug moiety (D) (or a peptide, polypeptide, protein or a tagging marker moiety) through preferably a linker (L), at for example one to twenty drug moieties to one antibody. Such a conjugated antibody may be made by means using a known organic chemical reaction and a reagent A conjugated antibody may also be made by a method other than the one above, and may be made, for example, as a fusion protein by a recombination technique, or by using a multispecific antibody, or by peptide synthesis.

"Polypeptide" means a peptide or protein containing more than about ten amino acids.

A polypeptide may be an antigen for an antibody. Moreover, antibodies against various polypeptides have been known to be useful in many fields such as medicine.

Polypeptides include mammalian polypeptides (in particular human polypeptides) and eukaryotic polypeptides, etc.; among which growth factors, hormones, cytokines, and receptors thereof, clotting factors and anti-clotting factors, etc. may be mentioned in particular as industrially useful.

While not restricted thereto, polypeptides include renin, growth hormones (such as human growth hormone and bovine growth hormone), growth hormone releasing factors, parathyroid hormone, thyroid-stimulating hormone, lipoproteins, α-1 anti-trypsin, insulin (λ chain and B chain), pro-insulin, follicle-stimulating hormone, calcitonin, luteinizing hormone, glucagon, Factor VIIIC, Factor IX, tissue factor, von Willebrand factor, protein C, atrial natriuretic factor, urokinase, t-pA, bombesin, thrombin, HGF, TNF-α, TNF-β, TNF-R (TNFR1 and TNFR2, etc.), TGF-α, TGF-β (TGF-β1, TGF-β2, TGF-β3, TGF-β4 and TGF-β5, etc.), enkephalinase, RANTES, MIPI-1, serum albumin, mullerian inhibiting substance, relaxin (λ chain and B chain), pro-relaxin, gonadotropic hormone, β-lactamase, DNase, inhibin, activing, VEGF, VEGFR, integrin, protein A, protein D, rheumatoid factor, BDNF, neurotrophin (NT-3, NT-4, NT-5 and NT-6, etc.), NGF-β, PDGF, fibroblast growth factor (aFGF and bFGF, etc.), EGF, EGFR, HER2, insulin-like growth factor (IGF-I and IGF-II, etc.), insulin-like growth factor binding protein, death receptor (DR3, DR4 and DR5, etc.), Fas ligand, Fas receptor, CD-3, CD-4, CD-8, CD-10, CD-11, CD-19, CD-20, CD-25, CD-32, CD-30, CD-33, CD-37, CD-52, HLA-DR, GPIIb, IgE, C5, CCR-4, α4-integrin, RANKL, CTLA4, Blys, NGEP, MUC-1, CEA, EpCAM, erythropoietin, BMP, immunotoxin, interferon (IFN-α, IFN-β and IFN-γ, etc.), colony stimulating factor (M-CSF, GM-CSF and G-CSF, etc.), interleukin (from IL-1 to IL-13, etc.), superoxide dismutase, T cell receptor, decay-accelerating factor, viral antigens (HIV envelope, etc.), antibodies and fragments of the above polypeptides.

"Polynucleotide" or "nucleic acid" means a nucleotide polymer of any length, and includes DNA and RNA. Nucleotides include deoxyribonucleotides, ribonucleotides, modified nucleotides (for example, methylated nucleotides) or bases, and/or analogs thereof. Nucleotides are connected by DNA or RNA polymerase or a synthetic reaction. A polynucleotide or nucleic acid may comprise a modification (for example, a linkage with a tag or a protection group) formed after connection of nucleotides. Moreover, "oligonucleotide" means a short, generally single-chain polynucleotide. While not restricted thereto, it may mean a synthetic polynucleotide of a length of less than about 200 nucleotides in general.

"Vector" means a nucleic acid molecule capable of transporting another nucleic acid. Vectors include plasmids (circular double-chain DNA linked to an additive DNA), phage vectors (phage linked to an additive polynucleotide) and viral vectors (virus linked to an added polynucleotide), etc. Some vectors can self-replicate in host cells to which they are introduced (for example, bacterial vectors with a bacterial replication origin and episomal mammalian vectors). Other vectors are integrated into the host cell genome when introduced into a host cell and replicate with the host genome (for example, non-episomal mammalian vectors). Further, some vectors can direct the expression of a gene operably linked thereto. Such vectors are called expression vectors or recombinant expression vectors. In general, expression vectors useful in recombinant DNA technology are often in the form of plasmids.

A polypeptide or nucleic acid having a certain sequence identity can comprise several amino acid/nucleotide mutations (changes) with respect to the amino acid/nucleotide sequence that forms the base. Such modifications are more desirable when they can improve the properties of the target molecule (for example, the binding affinity and/or biological property of an antibody). An amino acid sequence mutant of a polypeptide may be prepared by introducing an appropriate nucleotide mutation into the nucleic acid of the polypeptide or by peptide synthesis. Such a mutation includes a deletion and/or insertion and/or substitution of a residue in the amino acid sequence. The deletion, insertion and substitution may be in any combination so long as they are within such an extent that the target molecule retains the desired characteristic.

A method for introducing a mutation into a sequence, while not restricted thereto, may include isolation from a natural source (in cases of naturally occurring amino acid/nucleotide sequence mutants), site-specific mutation, PCR-induced mutation and cassette mutagenesis.

A polypeptide may be changed to increase or decrease the level of glycosylation. The glycosylation of a polypeptide is typically either by an N-link or an O-link. N-link means a linkage of a carbohydrate moiety to the side chain of an asparagine residue. The tripeptide sequences of asparagine- X-serine and asparagine-X-threonine (X is any amino acid other than proline) are the recognition sequences for enzymatic linkage of a sugar chain moiety to the asparagine side chain. Therefore, when any of these tripeptide sequences are present in a polypeptide, they become potential glycosylation sites. O-linked glycosylation means a linkage of one of the sugars, N-acetyl galactosamine, galactose or xylose, to a hydroxy amino acid, most commonly serine or threonine, though sometimes the linkage occurs to 5-hydroxyproline or 5-hydroxylysine.

The addition or deletion of a glycosylation site in a polypeptide may be achieved by changing the amino acid sequence such that one or more of the above tripeptide sequences (N-linked glycosylation sites) are made or deleted. The change may also be made by an addition, deletion or substitution of one or more serine or threonine residues in the polypeptide sequence that forms the base (in the case of O-linked glycosylation sites).

Additionally, a polypeptide having a certain amino acid sequence may include those wherein an oligosaccharide (sugar chain) linked to the polypeptide has been changed from the natural form.

Moreover, a preferable substitution of an amino acid residue is a conservative substitution, and examples thereof are shown in Table 2. It is possible to introduce such an amino acid substitution into a polypeptide, and screen the substitute for a desired activity/effect (for example, antigen binding, immunogenicity, ADCC or CDC).

A non-conservative substitution is an exchange of one of the members of one group with one in another group, and a non-conservative substitution is possible within such an extent that a desired characteristic is retained.

TABLE 2

| Original residue | Exemplary substitution residue | Preferable substitution residue |
|---|---|---|
| Ala (A) | Val, Leu, Ile | Val |
| Arg (R) | Lys, Gln, Asn | Lys |
| Asn (N) | Gln, His, Asp, Lys, Arg | Gln |
| Asp (D) | Glu, Asn | Glu |
| Cys (C) | Ser, Ala | Ser |
| Gln (Q) | Asn, Glu | Asn |
| Glu (E) | Asp, Gln | Asp |
| Gly (G) | Ala | Ala |
| His (H) | Asn, Gln, Lys, Arg | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Trp, Leu, Val, Ile, Ala, Tyr | Tyr |
| Pro (P) | Ala | Ala |
| Ser (S) | Thr | Thr |
| Thr (T) | Val, Ser | Ser |
| Trp (W) | Tyr, Phe | Tyr |
| Tyr (Y) | Trp, Phe, Thr, Ser | Phe |
| Val (V) | Ile, Leu, Met, Phe, Ala, norleucine | Leu |

Regarding antibody mutants, an amino acid in the complementarity determining region (CDR) and/or framework region (FR) of a parent antibody may be changed. While not restricted thereto, affinity maturation (for example, using phage display) may be given as a method for making a mutant from a parent antibody. Moreover, a mutant may be made by analyzing the crystal structure of an antigen-antibody complex and determining a candidate mutation site.

"Natural disulfide bond" refers to a cysteine-cysteine covalent bond usually present in a wild-type polypeptide (such as an antibody).

"Non-natural disulfide bond" refers to a cysteine-cysteine covalent bond formed at a position outside the above "natural disulfide bond".

Therefore, even when one of the cysteine residues forming a disulfide bond is a natural cysteine residue (a cysteine residue usually present in a wild-type polypeptide) and the other is a non-natural cysteine residue (a cysteine residue present at a position different from a natural cysteine residue), the overall disulfide bond may be regarded as a non-natural disulfide bond. For a non-natural disulfide bond, the two cysteine residues forming the disulfide bond are preferably both non-natural cysteine residues.

Additionally, in the present specification, unless particularly indicated, the description "disulfide bond" is used as a general name that includes both "natural disulfide bond" and "non-natural disulfide bond" so long as it is not against the object of the present invention.

A non-natural cysteine residue may be introduced by any method into a desired light chain or heavy chain, and all methods known in the relevant field may be used, so long as it is not against the object of the present invention. Specifically, a cysteine residue may be introduced by substituting an amino acid residue at a desired position with a cysteine residue, or by inserting a cysteine residue at a desired position. Such a substitution or insertion may be performed using a method for modifying an amino acid residue such as a known genetic modification technique.

Regarding natural disulfide bonds, based on the cross-linking mode, they are further separated into "intra-chain bonds", which are formed within the same polypeptide chains, and "inter-chain bonds", which are formed between heterologous polypeptide chains. For example, in the case of human IgG1 antibody, there is one of the former in each domain, and twelve in total are present in the entire molecule. On the other hand, as for the latter, there are two heavy chain-heavy chain bonds and one between each light chain-heavy chain pair. Therefore, in the case of human IgG1 antibody, there are a total of sixteen natural disulfide bonds per molecule. The number and positions of the natural disulfide bonds vary depending on the class or subclass of the antibody, and are inherent for each. For example, in the case of the light chain-heavy chain bonds in human IgG1 antibody, the disulfide bond is formed between the cysteine residue at amino acid position 214 of the CL region and the cysteine residue at amino acid position 220 of the CH1 region. In the case of the light chain-heavy chain bonds in IgG2, IgG3, IgG4 and IgM antibodies, the disulfide bond is formed between the cysteine residue at amino acid position 214 of the CL region and the cysteine residue at amino acid position 131 of the CH1 position.

"Forming a disulfide bond at a different position" (the position of the disulfide bond is different) means that when comparing two polypeptides or disulfide bonds present in portions thereof, the formation of a disulfide bond in one is in a pattern different from the other (there is a disulfide bond that is present in one but not present in the other). In this case, there may be identical (overlap) disulfide bonds between the two polypeptides or portions thereof (in particular, intra-chain bonds may be identical). From the point of reducing crosses of the two polypeptides or portions thereof, the number of identical disulfide bonds (except intra-chain bonds) is preferably 2, 1 or 0, and most preferably 0.

Additionally, regarding the similarities and differences between two disulfide bonds, when both of the two cysteine residues constituting each disulfide bond are identical or at corresponding positions, the bonds are regarded as the "same", and when at least one is at a substantially different position, the bonds are regarded as "different". In order to reduce crosses, both are preferably at different positions, though they are restricted thereto.

Moreover, as "amino acid residues not forming a disulfide bond", typically, amino acid residues other than cysteine and those where the SH group of a cysteine residue has been chemically modified to a state incapable of forming a disulfide bond may be given. By substituting a cysteine residue capable of forming a disulfide bond with these amino acid residues, it is possible to prevent the formation of a disulfide bond. A substitution to alanine or serine is often used when substituting a cysteine residue with an amino acid residue which does not form a disulfide bond.

Alternatively, when the function of a desired polypeptide can be retained, it is possible for a disulfide bond not to be formed due to deletion of a cysteine residue, and in this case, the cysteine residue may be changed to an "amino acid residue which does not form a disulfide bond".

"Purification" means the removal of impurities such that a target molecule is present in a sample at a concentration at least 95%, at least 98% or at least 99% by weight in the sample.

"Isolated" means that a target molecule is in a state of having been separated and/or recovered from at least one other similar molecule (polypeptide, nucleic acid or the like) that usually accompany the target molecule in a natural environment. Usually, an isolated molecule is prepared via at least one purification step. For a polypeptide, while not restricted thereto, for example, it may be regarded as sufficiently isolated when it has been purified (1) such that the purity when measured by the Lowry method exceeds 95% or 99 wt %, (2) such that it is enough to obtain at least 15 N-terminal or internal amino acid sequence residues by using an amino acid sequence determining device, or (3) such that it is homogeneous by SDS-PAGE under non-reducing or reducing conditions using Coomassie blue or silver staining.

"Composition" when used in the context of the present invention means either i) a composition comprising at least two antibodies, or ii) a composition comprising an antibody or another component, and unless clearly indicated, includes both embodiments. As a composition used in the meaning of i), for example, a cell co-expressing at least two antibodies in the same cell, or a composition prepared from the cell may be given. As for other components, any components may be used within the extent of not going against the object for which the composition is used, but it is particularly preferable to use a pharmaceutically acceptable carrier.

"Pharmaceutically acceptable carrier", while not restricted thereto, may include, for example, sterilized water or physiological saline, stabilizers, excipients, antioxidants (such as ascorbic acid), buffers (phosphoric acid, citric acid, other organic acids and salts thereof, etc.), preservatives, surfactants (polysorbate, polyethylene glycol, etc.), chelating agents (EDTA, etc.), binders, pH adjusters and cells (mammalian erythrocytes, etc.). Moreover, proteins (low molecular weight polypeptides, serum albumin, gelatin, immunoglobulin, etc.), amino acids (glycine, glutamine, asparagine, arginine, histidine, lysine, etc.) and salts thereof, saccharides such as monosaccharides (glucose, mannose, galactose, etc.) and polysaccharides (maltose, trehalose, maltotriose, dextrin, dextran, sucrose, etc.), sugar alcohols (mannitol and sorbitol, etc.), carbohydrates, synthetic polymers (polyolefin, polystyrene, styrene, divinylbenzene copolymer, polymethacrylate, polyamide, etc.) or natural polymers (cellulose, agarose, chitin, chitosan, etc.) and cross-linked bodies thereof may be included.

When making an aqueous solution for injection, an isotonic solution containing, for example, physiological saline, glucose or a supplement (D-sorbitol, D-mannose, D-mannitol, sodium chloride, etc.); an appropriate solubilizing agent (for example, an alcohol (ethanol, etc.), polyalcohol (propylene glycol, polyethylene glycol, etc.), non-ionic surfactant (polysorbate 20, polysorbate 80, polysorbate 120, polyoxyethylene hardened castor oil, etc.)) or the like may be used in combination. Moreover, it is also possible to enclose a bispecific antibody of the present invention with a microcapsule (a microcapsule of hydroxymethyl cellulose, gelatin, polymethyl methacrylic acid or the like) or to make it into a colloid drug delivery system (liposome, albumin microsphere, microemulsion, nanoparticle and nanocapsule, etc.) as necessary.

"At least one" means one or more, and includes two, three, four and five; or about 5% (or more), about 10% (or more), about 20% (or more), about 50% (or more) and about 80% (or more) of a theoretical upper limit for the combination. The upper limit may be appropriately determined by those skilled in the art within the extent not compromising the object of the present invention or the effect of the invention or the like. Such an upper limit includes two, three, four and five; or about 5% (or more), about 10% (or more), about 20% (or more), about 50% (or more), about 80% (or more) and 100% of a theoretical upper limit for the combination. "At least two" is when the lower limit of "at least one" is two, not one; and the same applies to the others.

EMBODIMENTS

The present invention will be described in detail below by referring to specific embodiments, but the present invention is not restricted thereto.

These aspects may be used alone or in combination. Additionally, see the above "Description of Terminology and Aspects" for the definition and details of each aspect.

The present invention relates to a method of restricting a light chain-heavy chain pairing by changing the position at which a disulfide bond is formed, and enables efficient production of an antibody comprising a light chain and a heavy chain when there are multiple light chain and heavy chain combinations (see FIG. 1).

One embodiment of the present invention is a method for making an antibody comprising at least two different Fab regions; or a composition comprising at least two antibodies comprising Fab regions, the Fab regions being different between the at least two antibodies; the method comprising:

i) a step of culturing a host cell comprising a nucleic acid encoding said antibody or antibodies under conditions to express said antibody, and ii) a step of recovering said antibody or antibodies from the host cell culture, wherein said nucleic acid encodes at least one region comprising a cysteine residue which forms a non-natural disulfide bond between a light chain and a heavy chain of said Fab region, wherein due to the presence of said non-natural disulfide bond, the position of a disulfide bond between a light chain and a heavy chain in a Fab region is different from the position of a disulfide bond between a light chain and a heavy chain in at least one other Fab region.

In one embodiment, the above non-natural disulfide bond and the above disulfide bond in the above method are disulfide bonds between a CL region and a CH1 region.

Additionally, one embodiment of the present invention is a method for making an antibody comprising a first Fab region which comprises a first light chain and heavy chain, and a second Fab region which comprises a second light chain and heavy chain each being different from said first light chain and heavy chain; the method comprising:

a) a step of substituting at least one amino acid residue other than cysteine in a CL region and a CH1 region in the first Fab region of a parent antibody of said antibody with a cysteine residue which forms a disulfide bond, and b) a step of forming a non-natural disulfide bond in the first Fab region by said cysteine residue which forms a disulfide bond, wherein due to the presence of said non-natural disulfide bond, the first Fab region forms a disulfide bond at a position different from the second Fab region.

Moreover, another embodiment of the present invention is an antibody comprising at least two different Fab regions, wherein at least one Fab region comprises a cysteine residue which forms a non-natural disulfide bond between a CL region and a CH1 region, thereby forming a non-natural disulfide bond, wherein due to the presence of said non-natural disulfide, the position of a disulfide bond between a CL region and a CH1 region in a Fab region is different from the position of a disulfide bond between a CL region and a CH1 region in at least one other Fab region.

In one embodiment, the above antibody comprises two different Fab regions.

Furthermore, another embodiment of the present invention is a composition comprising at least two antibodies comprising Fab regions, the Fab regions being different between the at least two antibodies, wherein at least one Fab region comprises a cysteine residue which forms a non-natural disulfide bond between a light chain and a heavy chain, thereby forming a non-natural disulfide bond, wherein due to the presence of said non-natural disulfide bond, the position of a disulfide bond between a light chain and a heavy chain of a Fab region is different from the position of a disulfide bond between a light chain and a heavy chain of at least one other Fab region.

In one embodiment, the above non-natural disulfide bond and the above disulfide bond in the above composition are disulfide bonds between a CL region and a CH1 region.

Typically, the above antibodies or composition may be made by the aforementioned method for making an antibody or composition.

According to the present invention, restriction of the light chain-heavy chain combination in respective Fab regions reduces the yields of antibodies of unwanted combinations caused by the aforementioned randomness in combination, and thus it is possible to efficiently make an antibody comprising at least two different Fab regions (an antibody comprising a first Fab region and a second Fab region) or a composition comprising at least two antibodies comprising different Fab regions.

In the present invention, by forming a light chain-heavy chain (particularly CL region-CH1 region) non-natural disulfide bond, the positions of light chain-heavy chain (particularly CL region-CH1 region) disulfide bonds are not completely identical between two Fab regions (between a first light chain and heavy chain and a second light chain and heavy chain). By doing so, the CL region-CH1 region bonds are preferably specific to each Fab region. In order to make the disulfide bonds not completely identical between two Fab regions, a part of a CL region-CH1 region disulfide bond in one Fab region is made non-natural (a natural disulfide bond in one and a non-natural disulfide bond in the other), or a non-natural disulfide bond is formed in one at a position different from a non-natural disulfide bond in the other (both are non-natural disulfide bonds).

Moreover, it is more preferable for the CH1 region-CL region disulfide bonds not to cross between at least two different Fab regions, or for a disulfide bond to form at a position which reduces such crosses by combination.

Additionally, it is more preferable for a disulfide bond not to form between a first light chain and a second heavy chain or between a second light chain and a first heavy chain, or for a disulfide bond to form at a position which reduces such crosses by combination.

One embodiment of the present invention is any of the above method, antibody and composition, wherein the position of a disulfide bond between a CL region and a CH1 region in one Fab region is entirely different from the position of a disulfide bond between a CL region and a CH1 region in at least one other Fab region.

The position of an amino acid residue capable of forming a non-natural disulfide bond by substitution to a cysteine residue or the position at which to form a non-natural disulfide bond with few crosses is determined based on the conformational information of a desired antibody that is to be formed. In most cases, conformational information describing the necessary coordinates of each atom is available free of charge from public databases such as Protein Data Bank (PDB). The obtained coordinate information enables a conformation to be calculated by using specialized software generally called computational chemistry software, and a virtual visual projection on a PC monitor or the like is possible. Additionally, the distance and bond angle between any atoms, and further the binding energy, etc., can be calculated by computational chemistry software in most cases. A natural disulfide bond present in an antibody molecule is a covalent bond between the sulfur atoms present at the side chain termini of cysteine residues, and when bearing an inter-chain bond, it is predicted that the directions of the side chains will tend to face one another. To reflect this in a conformational calculation, it is appropriate to set the calculation with the condition of the distance between the (3 carbons of two cysteine residues being smaller than the a carbons of the same.

For example, in the case of the light chain-heavy chain bonds of human IgG1 antibody, with the disulfide bond formed between the cysteine residue at amino acid position 214 of the CL region and the cysteine residue at amino acid position 220 of the CH1 region, the distance between the above α carbons ($C_\alpha$-$C_{\alpha'}$) is calculated to be 4.441 Å, and the distance between the above β carbons ($C_\beta$-$C_{\beta'}$) 3.832 Å (PDB entry: 1L7I).

In view of these results and known information relating to disulfide bonds, for example, if $C_\alpha$-$C_{\alpha'}$ is set to be 7.0 Å or below, $C_\beta$-$C_{\beta'}$ 5.5 Å or below and the distance between β carbons <the distance between a carbons, and amino acid residue pairs satisfying the conditions are selected from amino acid residue groups present in adjacent peptide chains based on calculations, that is, those amino acid residue pairs may be potential candidates for substitutions to cysteine residues. Values used in calculations for $C_\alpha$-$C_{\alpha'}$ and $C_\beta$-$C_{\beta'}$ are not restricted to the above values, and for example, respective values of 7.5 Å or below, 8 Å or below, 8.5 Å or below, 9 Å or below, 9.5 Å or 10 Å or below, and 6 Å or below, 6.5 Å or below, 7 Å or below, 7.5 Å or below, 8 Å or below or 8.5 Å or below may be used in combination.

Additionally, the method for modifying an amino acid residue used to carry out the present invention is not particularly restricted, and all methods capable of achieving the object may be used. An amino acid residue modification in the present invention is typically performed by substitution/deletion/addition of a cysteine residue by modifying the nucleic acid encoding the amino acid at a desired position. However, it is not restricted thereto, and may be a cysteine residue modification by chemical modification or the like. Moreover, "substitution of an amino acid residue" naturally includes substituting a nucleic acid encoding an amino acid residue and the resulting substitution of the amino acid residue. A substitution to an alanine residue or serine residue is often used when substituting a cysteine residue with an amino acid residue which does not form a disulfide bond.

Furthermore, since the present invention is not restricted by a specific CDR sequence or the like, the antibody which is the object of the present invention may have a Fab region corresponding to an antibody against any antigen.

As positions at which a non-natural disulfide bond forms easily, while not restricted thereto, examples may include (1) between light chain position 116-heavy chain position 126, light chain position 116-heavy chain position 127, light chain position 116-heavy chain position 128, light chain position 116-heavy chain position 134, light chain position 116-heavy chain position 141, light chain position 118-heavy chain position 126, light chain position 118-heavy chain position 127, light chain position 118-heavy chain position 128, light chain position 118-heavy chain position 134, light chain position 118-heavy chain position 141, light chain position 121-heavy chain position 126, light chain position 121-heavy chain position 127, light chain position 121-heavy chain position 128, light chain position 121-heavy chain position 134, light chain position 121-heavy chain position 141, light chain position 124-heavy chain position 126, light chain position 124-heavy chain position 127, light chain position 124-heavy chain position 128, light chain position 124-heavy chain position 134, or light chain position 124-heavy chain position 141; and (2) between light chain position 162-heavy chain position 170, light chain position 162-heavy chain position 171 or light chain position 162-heavy chain position 173.

As more specific combinations of positions at which a non-natural disulfide bond forms easily, while not restricted thereto, examples may include between a) light chain position 116-heavy chain position 134, b) light chain position 116-heavy chain position 141, c) light chain position 118-heavy chain position 128, d) light chain position 121-heavy chain position 126, e) light chain position 121-heavy chain position 127, f) light chain position 124-heavy chain position 126, g) light chain position 162-heavy chain position 170, h) light chain position 162-heavy chain position 171 and i) light chain position 162-heavy chain position 173. Cysteine residues introduced into these positions are present in relatively close positions and side chain directions, and can form disulfide bonds. More preferably, when the light chain is a λ chain, examples may include between c) light chain position 118-heavy chain position 128, f) light chain 124-heavy chain position 126, g) light chain position 162-heavy chain position 170, h) light chain position 162-heavy chain position 171 and i) light chain position 162-heavy chain position 173.

A non-natural disulfide bond is more preferably formed by a cysteine residue introduced at at least one set of light chain-heavy chain positions selected from a) light chain position 116-heavy chain position 134, b) light chain position 116-heavy chain position 141, c) light chain position 118-heavy chain position 128, f) light chain position 124-heavy chain position 126, g) light chain position 162-heavy chain position 170, h) light chain position 162-heavy chain position 171 and i) light chain position 162-heavy chain position 173. At these positions, it is more certain that a cysteine residue introduced into the light chain will not cross with the cysteine residue at position 220 of the heavy chain. When the light chain is a λ chain, a non-natural disulfide bond is further more preferably formed by a cysteine residue introduced at a position other than between f) light chain position 124-heavy chain position 126, further more preferably formed by a cysteine residue introduced at c) light chain position 118-heavy chain position 128, g) light chain position 162-heavy chain position 170, h) light chain position 162-heavy chain position 171 or i) light chain position 162-heavy chain position 173.

A non-natural disulfide bond is more preferably formed by a cysteine residue introduced at at least one set of light chain-heavy chain positions selected from b) light chain position 116-heavy chain position 141, c) light chain position 118-heavy chain position 128, d) light chain position 121-heavy chain position 126, e) light chain position 121-heavy chain position 127, f) light chain position 124-heavy chain position 126, g) light chain position 162-heavy chain position 170, h) light chain position 162-heavy chain position 171 and i) light chain position 162-heavy chain position 173. At these positions, it is more certain that a cysteine residue introduced into the heavy chain will not cross with the cysteine residue at position 214 of the light chain. When the light chain is a λ chain, a non-natural disulfide bond is further more preferably formed by a cysteine residue introduced at c) light chain position 118-heavy chain position 128, f) light chain position 124-heavy chain position 126, g) light chain position 162-heavy chain position 170, h) light chain position 162-heavy chain position 171 or i) light chain position 162-heavy chain position 173.

A non-natural disulfide bond is further more preferably formed by a cysteine residue introduced at at least one set of light chain-heavy chain positions selected from b) light chain position 116-heavy chain position 141, c) light chain position 118-heavy chain position 128, f) light chain position 124-heavy chain position 126, g) light chain position 162-heavy chain position 170, h) light chain position 162-heavy chain position 171 and i) light chain position 162-heavy chain position 173. A cysteine residue introduced at these positions will more certainly not cross with a natural disulfide bond. When the light chain is a λ chain, a non-natural disulfide bond is further more preferably formed by a cysteine residue introduced at a position other than between f) light chain position 124-heavy chain position 126.

A non-natural disulfide bond is further more preferably formed by a cysteine residue introduced at at least one set of light chain-heavy chain positions selected from between b) light chain position 116-heavy chain position 141, f) light chain position 124-heavy chain position 126, g) light chain position 162-heavy chain position 170, h) light chain position 162-heavy chain position 171 and i) light chain position 162-heavy chain position 173. When a cysteine residue is introduced at these positions to carry out the present invention, very superior yield and cross-reactivity can be achieved. Even more preferably, when the light chain is a κ chain, a non-natural disulfide bond is formed by a cysteine residue introduced at b) light chain position 116-heavy chain position 141, f) light chain position 124-heavy chain position 126 or g) light chain position 162-heavy chain position 170; and when the light chain is a λ chain, a non-natural disulfide bond is formed by a cysteine residue introduced at h) light chain position 162-heavy chain position 171 and i) light chain position 162-heavy chain position 173. Moreover, when considering the convenience of purification, a non-natural disulfide bond is even more preferably formed between f) light chain position 124-heavy chain position 126 or between i) light chain position 162-heavy chain position 173, and most preferably formed between f) light chain position 124-heavy chain position 126.

In the embodiment of this paragraph, when the light chain is a λ chain, a non-natural disulfide bond is more preferably formed by a cysteine residue introduced at a position other than between f) light chain position 124-heavy chain position 126.

Regarding the introduction of a cysteine residue into the above positions, while not restricted thereto, a cysteine substitution or insertion at the following positions, or a substitution or insertion by cysteine of the following amino acids may be given as examples.

Light chain (κ chain): position 116 (F116C), position 118 (F118C), position 121 (S121C), position 124 (Q124C), position 162 (S162C)

Light chain (λ chain): position 118 (F118C), position 124 (E124C), position 162 (T162C) Heavy chain: position 126 (F126C), position 127 (P127C), position 128 (L128 C), position 134 (S134C), position 141 (A141C), position 170 (F170C), position 171 (P171C), position 173 (V173C)

Additionally, a further embodiment of the present invention is any of the above method, antibody and composition, wherein a natural disulfide bond is not formed between a CL region and CH1 region of at least one Fab region, or at least one Fab region does not comprise a cysteine residue which can form a natural disulfide bond between a light chain and a heavy chain. In this embodiment, a natural disulfide bond is not formed, and instead a light chain-heavy chain bond is formed through only a non-natural disulfide bond in at least one Fab region. At this time, a natural disulfide bond or another non-natural disulfide bond may be formed in another Fab region.

An example of a natural disulfide bond, while not restricted thereto, is the disulfide bond between the cysteine residue at amino acid position 214 of the light chain and the cysteine residue at amino acid position 220 of the heavy chain.

The method, antibody or composition in any of the above embodiments may further be a method comprising a step for applying a technique for restricting a heavy chain-heavy chain combination, or an antibody or composition made thereby. Such techniques, while not restricted thereto, include the knobs-into-holes technique (for example, U.S. Pat. No. 7,183,076; WO 98/50431 (JP Patent No. 4324231)), heterologous bonds by electrostatic attraction (for example, WO 2009/089004, WO 2007/147901), heterologous bonds by charged leucine zipper (for example, WO 2011/034605), efficient production method by light chain heavy chain exchange expression (for example, WO 2009/0802513) and purification by protein A affinity chromatography (WO 2010/151792). Any of these techniques may be used in combination with the present invention, and in that case, they are also included in the technical scope of the present invention. When combining these techniques with the present invention, it is possible to make a light chain-heavy chain and heavy chain-heavy chain restricted antibody or composition (for example, a multispecific antibody) very efficiently.

Moreover, a further embodiment of the present invention is the method, antibody or composition of any of the above embodiments, wherein the antibody is a multispecific antibody (particularly a bispecific antibody).

As a method for making a multispecific antibody, the hybrid-hybridoma technique (Milstein and Cuello, *Nature* 305: 537-539 (1983)) is known. In this method, since the light chain and heavy chain of an immunoglobulin are randomly combined, in the case of a bispecific antibody, it is possible for these hybridomas (quadromas) to produce mixtures of ten different antibody molecules. Only one of these has the correct bispecific structure, so the yield of the desired bispecific antibody by this method is low (see FIG. 1). Additionally, while affinity chromatography or the like is used to purify a desired multispecific antibody, generally, it is not easy to increase the purity of a desired multispecific antibody.

Furthermore, while there are several known techniques aimed at overcoming the difficulties caused by random light chain and heavy chain combinations in the production of a multispecific antibody, many restrict heavy chain-heavy chain bonds.

In contrast, the present invention relates to a method for restricting a light chain-heavy chain bond by changing a disulfide bond, and enables efficient production of a multispecific antibody by a mechanism different from conventional improvements. Therefore, it is possible to use a conventional art such as a method for restricting a heavy chain-heavy chain pairing in combination, and in that case, a multispecific antibody can be made even more efficiently.

Moreover, a further embodiment of the present invention is the method, antibody or composition of any of the above embodiments, wherein the antibody is one wherein at least two antibody fragments are connected through a linker or directly.

Additionally, a further embodiment of the present invention is the method, antibody or composition of any of the above embodiments, wherein the antibody is an antibody fragment. In the case of applying the present invention to make a single antibody fragment, an antibody fragment comprising at least two pairs of combinations of a light chain moiety and a heavy chain moiety is preferred, and while not restricted thereto, such an antibody fragment includes F(ab')$_2$. Furthermore, in the case of applying the present invention to make a composition comprising an antibody fragment, a composition comprising at least one pair of a light chain moiety and a heavy chain moiety is preferred, and while not restricted thereto, such a composition includes a composition comprising Fv, Fab, F(ab')$_2$.

The antibody, by being an antibody fragment, is superior in its productivity and is superior in the migration/infiltration for a tissue or lesion expressing a target molecule.

Moreover, a further embodiment of the present invention is the method, antibody or composition of any of the above embodiments, wherein a Fc region of the antibody is substituted with another molecule. When the object of the present invention is an antibody, the antibody may have a Fc region. Additionary, the Fc region may take any structure within an extent not going against the object of the present invention. In other words, the antibody of the present invention not only includes an antibody with a mutated Fc region, but also an antibody molecule in a broad sense wherein the Fc region has been substituted with a molecule other than a normal Fc region. Depending on the use/purpose of the antibody, it is known that many molecules may be used as the substitution molecule, and examples may include polynucleotides, nucleotides, polypeptides, peptides, polyethylene glycols, amino acids (for example, glycine, histidine), saccharides, low molecular weight compounds, lipids, phospholipids (for example, lecithin), vitamins (for example, biotin) and enzymes.

Additionally, a further embodiment of the present invention is the method, antibody or composition of any of the above embodiments, wherein the antibody is an IgG1, IgG2, IgG3, IgG4 or IgM antibody.

Moreover, a further embodiment of the present invention is the method, antibody or composition of any of the above embodiments, wherein the light chain of the antibody is a κ chain.

A further embodiment of the present invention is the method, antibody or composition of any of the above embodiments, wherein the antibody is a chimeric antibody, humanized antibody or human antibody. The chimeric antibody, humanized antibody or human antibody may be any of the aforementioned chimeric antibody, humanized antibody or human antibody within an extent not compromising the effect of the invention. Preferably, the antibody is a human antibody. By being a human antibody, the effects of antigenicity reduction and in vivo kinetics improvement are provided. Additionally, by targeting a human antibody, the information described in the present specification may also be applied to the fullest extent.

A further embodiment of the present invention is the method of any of the above embodiments, wherein the host cell is an eukaryotic cell or *E. coli*. The present invention does not relate to a host cell-dependent method, so any host cell suitable for antibody production may be used. Moreover, as host cells commonly used in antibody production, eukaryotic cells or *E. coli* may be suitably used. While not restricted thereto, examples of eukaryotic cells may include nucleated cells derived from yeasts, fungi, insects, plants, animals, human or other multicellular organisms.

A common method for making an antibody shall be briefly described below.

The method of any of the above embodiments may further comprise one or more of the steps or embodiments described in detail below.

(1) Immunization

Immunization is performed by administering an obtained antigen to a mammal. The antigen may be used in mixture with an adjuvant. As the mammal, a mouse is suitable, and a BALB/c mouse is more suitable. Immunization may be performed once or multiple times on the same mammal.

(2) Screening

Hybridomas are made by a usual method in spleen cells, and screening is performed using a desired activity such as antibody titer as an indicator. Before obtaining the spleen cells, a pre-screening may be performed using a serum activity such as serum antibody titer as an indicator per immunized mammal. The screening is preferably performed using ELISA.

(3) Mass production

A hybridoma selected by screening is administered to the peritoneal cavity of a mouse to induce ascites, and the antibody-containing ascitic fluid is collected and purified to obtain antibodies. Preferably, a SCID mouse is used as the mouse. As for purification, chromatography is preferably used, and affinity chromatography is more preferable. For example, protein G affinity chromatography is used.

(4) Recombinant production

Regarding an antibody obtained by screening, by obtaining cDNA from a hybridoma producing the antibody or the like, a recombinant can be made in another cell, and such an embodiment is also included in the above production method. Details of the method for making a recombinant in another cell using the obtained cDNA shall be described later.

One embodiment of the present invention is a nucleic acid encoding the antibody of any of the above embodiments. The nucleic acid is preferably DNA.

The nucleic acid of any of the above embodiments may be isolated and sequenced by a conventional method. While not restricted thereto, for example, sequencing may be performed using an oligonucleotide primer designed to specifically amplify a light chain and/or heavy chain, etc. Moreover, an isolated nucleic acid may be gene transferred into a prokaryotic or eukaryotic cell for cloning and expression. For such a process, reference may be made, for example, to *Molecular Cloning: A Laboratory Manual* (CSHL Press), *Current Protocols in Molecular Biology* (John Wiley & Sons, Inc.), *Antibody Engineering* (Springer), *Antibodies: A Laboratory Manual* (CSHL Press).

Additionally, one embodiment of the present invention is a vector comprising the nucleic acid of any of the above embodiments. Typically, this vector may be obtained by inserting the isolated nucleic acid of any of the above embodiments into a vector by a conventional method. The vector is preferably a replicable vector, and is more preferably a vector having a promoter (expression vector). While not restricted thereto, the vector generally comprises one or more components among a signal sequence, a replication origin, one or more selector genes, a promoter, an enhancer element and a terminator sequence. Each component shall be described below.

(1) Signal sequence

A desired polypeptide may be produced not only by a direct recombination method, but also as a fusion peptide with a signal sequence or the like. A signal sequence is something that is recognized and processed by a host cell (i.e., cleaved by signal peptidase). In a prokaryotic host cell, for example, a prokaryotic signal sequence such as alkaline phosphatase, penicillinase, lpp or heat-stable enterotoxin II leader may be used as the signal sequence. In yeasts, for example, yeast invertase leader, a factor leader, acid phosphatase leader, glucoamylase leader, or a signal described in WO 90/13646 may be used as the signal sequence. In a mammalian cell, for example, a virus secretion leader such as herpes simplex gD signal, or a mammalian signal sequence may be used.

(2) Replication Origin

Many vectors (for example, expression vectors or cloning vectors) comprise a nucleic acid sequence enabling vector replication in one or more selected host cells. In general, in a cloning vector, this sequence enables the vector to replicate independently from the host chromosomal DNA, and comprises a replication origin or autonomous replication sequence. Such sequences are well known for many bacteria, yeasts and viruses. The replication origin derived from plasmid pBR322 is suitable for most gram negative bacteria, the 2μ plasmid origin is suitable for yeasts, and various virus origins (SV40, polyoma, adenovirus, VSV, BPV, etc.) are useful for cloning vectors in mammalian cells. In general, a mammalian expression vector does not need a replication origin (in fact, the SV40 origin is typically often used as a promotor).

(3) Selector Gene

Many vectors (for example, expression vectors or cloning vectors) typically comprise a selector gene that is also called a selectable marker. As a typical selector gene, (a) a gene that provides resistance to an antibiotic or another toxin such as ampicillin, neomycin, methotrexate or tetracyclin; (b) a gene that complements auxotrophic deficiency; or (c) a gene that supplies an important nutrient that cannot be obtained from (a specific) medium (for example, D-alanine racemase for *Bacillus*) may be given.

(4) Promoter

Many vectors (for example, expression vectors or cloning vectors) generally comprise a promoter that is recognized by a host organism and is upstream of a nucleic acid encoding a desired polypeptide. As promoters suitable for use in a prokaryotic host, phoA promoter, β lactamase and lactose promoters, alkaline phosphase, tryptophan (trp) promoters, and hybrid promoters (for example, tac promoter) may be given. However, other bacterial promoters are also suitable. For example, a vector used in a bacterial system comprises a Shine-Dalgarno (S. D.) sequence upstream of a nucleic acid encoding a polypeptide. Moreover, promotor sequences for eukaryotic organisms are also known. Substantially all eukaryotic genes have an AT-rich region found about 25 to 30 bases upstream of the transcription start site of many genes. Another sequence found 70 to 80 bases upstream of the transcription start site of many genes is a CNCAAT region where N is any nucleotide.

The 3' terminus of most eukaryotic genes have an AATAAA sequence which is a signal that adds poly-A to the mRNA 3' terminus. These sequences may be suitably inserted into the expression vector of a eukaryotic organism.

(5) Enhancer Element

DNA transcription is often enhanced by an insertion of an enhancer sequence in a vector. Many enhancer sequences derived from mammalian genes are now known (globin, elastase, albumin, α-fetoprotein and insulin). However, typically, enhancers derived from eukaryotic cell viruses are often used. Examples include SV40 enhancer (100-270 base pairs) on the late side of the replication origin, cytomegalovirus early promoter enhancer, polyoma enhancer on the late side of the replication origin and adenovirus enhancer (see also Yaniv, *Nature*, 297: 17-18 (1982)). An enhancer may be inserted into a vector at the 5' or 3' of a polypeptide coding sequence, but is preferably located at a 5' position.

(6) Terminator Sequence

Many vectors (for example, expression vectors) used in eukaryotic host cells (nucleated cells derived from yeasts, fungi, insects, plants, animals, human or other multicellular organisms) may comprise a sequence necessary to terminate transcription and stabilize mRNA. Such a sequence can generally be obtained from a 5', sometimes 3', untranslated region of eukaryotic or viral DNA or cDNA. Regarding these regions, the untranslated portion of a polypeptide-coding mRNA comprises a nucleotide fragment that is transcribed as a polyadenylation fragment. One useful terminator sequence is bovine growth hormone polyadenylation region (for example, see WO 94/11026).

Usually, by transfecting the nucleic acid of any of the above embodiments into a host cell that does not produce antibodies (for example, *E. coli*, simian COS cell, Chinese hamster ovary (CHO) cell or myeloma cell) and culturing in an appropriate nutrient medium, the antibody encoded by the nucleic acid may also be produced (for example, see Skerra et al., *Curr. Opinion in Immunol.*, 5: 256-262 (1993); Pluckthun, *Immunol. Rev.* 130: 151-188 (1992)). Then, for example, by separating the antibody to a soluble fraction from a host cell paste and purifying it (for example, using a protein A or G column depending on the isotype), the antibody may be made.

The host cell may be cultured in various media. Among commercially available media, for example, Ham F10 (Sigma), MEM (Sigma), RPMI-1640 (Sigma) and DMEM (Sigma) are suitable for culturing host cells. These media may be supplemented as necessary with a hormone and/or another growth factor (for example, insulin, transferrin, epidermal growth factor), salt (for example, phosphate, magnesium, calcium, sodium chloride), buffer (for example, HEPES), nucleoside (for example, adenosine, thymidine), antibiotic (for example, gentamycin), trace element (such as an inorganic compound usually present at a final concentration in a micromolar range) and glucose or an equivalent energy source. Other necessary supplements may also be included at appropriate concentrations known to those skilled in the art. Suitable culture conditions, for example, temperature, pH, for each host cell are clear to those skilled in the art, or are within the range of simple examination of conditions.

When using the recombination technique, the antibody is produced in the cell or periplasmic space, or is directly secreted into the medium.

When the antibody is produced in the cell, the first step is to remove unwanted substances (such as cell fragments) by, for example, centrifugation or ultrafiltration. Carter et al., *Bio/Technology* (*NY*) 10: 163-167 (1992) describes a method for isolating an antibody secreted into a periplasmic space of *E. coli*. Briefly, a cell paste is cold thawed for about 30 minutes in the presence of sodium acetate (pH 3.5), EDTA and phenylmethylsulfonyl fluoride (PMSF). Cell debris can be removed by centrifugation.

When the antibody is secreted into the medium, a supernatant from such an expression system is generally concentrated using a protein concentration filter (for example, Amicon or Pellicon ultrafilter). Antibody degradation may be inhibited by including a protease inhibitor such as PMSF in any of the above steps, and the growth of exogenous contaminating organisms may be prevented by using an antibiotic.

An antibody composition prepared from a cell may be purified using, for example, hydroxyapatite chromatography, hydrophobic interaction chromatography, gel electrophoresis, dialysis and affinity chromatography. Typically, affinity chromatography is a preferred purification step. The suitability of protein A/G as the affinity ligand depends on the species and isotype of the immunoglobulin Fc region present in the antibody. Protein A can be used for the purification of antibodies based on human γ1, γ2 or γ4 heavy chain (for example, see Lindmark et al., *J. Immunol. Methods* 62: 1-13 (1983)). Protein G can be suitably used for all human γ heavy chains including all mouse isotypes and human γ3 (for example, see Guss et al., *EMBO J.* 5: 1567-1575 (1986)). Agarose is the most common matrix to which the affinity ligand is bound, but other materials can also be used. A mechanically stable matrix such as a controlled pore glass or poly(styrene divinyl)benzene enables a faster flow and shorter process time than what can be achieved with agarose. When an antibody comprises a CH3 domain, Bakerbond ABX resin (J. T. Baker, Phillipsburg, N.J.) is useful in purification. Fractionation with an ion exchange column, ethanol precipitation, reverse phase HPLC, chromatography with silica, chromatography with heparin, chromatofocusing, SDS-PAGE, and ammonium sulfate precipitation can also be used depending on the antibody to be collected.

Following the above preliminary purification steps, the mixture solution containing the desired antibody and a mixture may be subjected to, for example, a low pH hydrophobic interaction chromatography using an elution buffer of preferably a low salt concentration (for example, about 0-0.25 M NaCl), about pH 2.4-4.5.

OTHER EMBODIMENTS

The antibody of any of the above embodiments may be made into a composition or formulation or the like with optionally a pharmaceutically acceptable carrier or the like. Moreover, the antibody of any of the above embodiments can be applied to all sorts of uses for which antibodies are generally used.

Examples of representative uses for which a multispecific antibody is used are provided below.

[Detection/Diagnosis]

A multispecific antibody can be advantageously used in known assays, such as competitive binding assay, direct and indirect sandwich assay, and immunoprecipitation.

Additionally, a multispecific antibody can also be used to immobilize an enzyme used in an enzyme immunoassay. By designing one Fab region of a multispecific antibody to bind to a specific epitope on the surface of an enzyme without causing enzyme inhibition, and binding the other Fab region to an immobilization matrix to assure a high enzyme density at a desired site, an enzyme immunoassay can be carried out with good sensitivity.

A multispecific antibody can also be used for the in vivo immunodiagnosis or in vitro immunodiagnosis of various diseases such as tumors (Songsivilai et al., *Clin. Exp. Immunol.* 79: 315-321 (1990)). In that case, one Fab region of a multispecific antibody can bind to a tumor associated antigen, and the other Fab region can bind to a detectable marker such as a chelating agent binding to a radionuclide.

[Disease Treatment]

A multispecific antibody may be therapeutically useful by providing one Fab region that binds to a target cell (for example, a specific organ) and another Fab region that binds to a drug or the like (low molecular weight drug, polypeptide or the like) to deliver the drug or the like specific to the target cell.

Moreover, a multispecific antibody may be therapeutically useful by providing one Fab region that binds to a target (for example, a pathogen or tumor cell) and another Fab region that binds to a cytotoxicity-inducing factor molecule such as a T cell receptor or Fcγ receptor to restrict the target of cytotoxicity. In that case, a multispecific antibody can be used to specifically direct the cellular immune defense mechanism of a subject to a tumor cell or infectious pathogen.

Furthermore, a multispecific antibody may be therapeutically useful by providing one Fab region that binds to an antigen (for example, a membrane protein, receptor protein) on a target (for example, a pathogen or tumor cell) and another Fab region that binds to another antigen on the same target or the same type of target to change the strength of cytotoxicity (for example, ADCC improvement, apoptosis induction).

Additionally, a multispecific antibody can be used as a fibrin solvent or vaccine adjuvant. Further, these antibodies can be used in the treatment of infectious diseases (for example, for targeting an effector cell to a cell infected with a virus such as HIV virus or influenza virus or a protozoan such as *Toxoplasma gondii*), or can be used to deliver an immunotoxin to a tumor cell or to target an immunocomplex to a cell surface receptor.

Embodiments of the present invention have been described above, but these are exemplifications of the present invention, and various constitutions other than the above can be adopted.

For example, the present invention is useful when chemically linking a polypeptide chain having a structure satisfying the conditions of the present invention in vitro, or when wanting to increase specific light chain-heavy chain bonds (when making a multispecific antibody) or the like, and such methods are also included in the embodiments of the present invention.

EXAMPLES

The present invention shall be explained with examples below, but the present invention is not restricted by these examples. Moreover, the commercially available reagents mentioned in the examples were used according to the manufacturer's instructions or a conventional method unless particularly indicated.

The examples shall first show that mutants wherein a non-natural disulfide (Cys1m) was introduced are equal to the wild-type with respect to the molecular weight and function. Next, they shall show that the non-natural disulfide bond has high bond selectivity, i.e., not crossing with a natural disulfide bond. Lastly, they shall demonstrate based on various analysis results that by using Cys1m, a bispecific antibody in the complete form of an IgG antibody can be easily made.

Example 1

[Construction of Expression Vectors]

Figure 4:
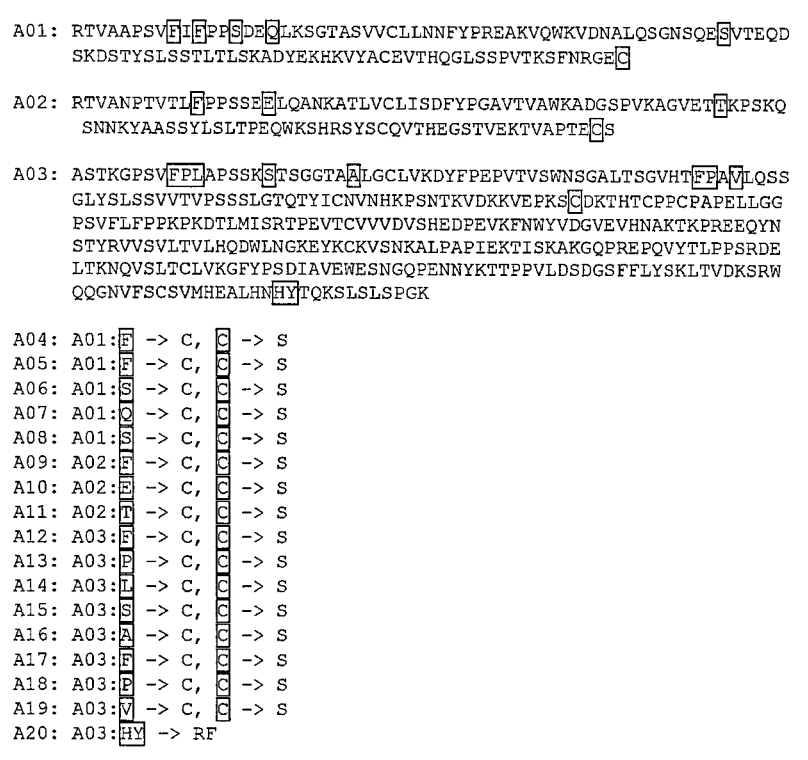

A commercially available expression vector pcDNA3.1 (+) (Invitrogen) was used as the vector for expressing various antibody molecules. A light chain expression unit (promoter, desired gene, polyA sequence) and a heavy chain expression unit (same) were arranged in tandem on one vector such that the gene transfer of a single vector was able to express an antibody. The base sequences of the primers used and cDNA obtained by cloning are shown in FIG. 2 and FIG. 3, and the amino acid sequences of the transcripts are shown in FIG. 4. FIG. 2 shows, in order from top to bottom, SEQ ID NO: 1 to SEQ ID NO: 47. That is, P01 to P47 in FIG. 2 correspond to SEQ ID NO: 1 to SEQ ID NO: 47, respectively. FIG. 3 shows, in order from top to bottom, SEQ ID NO: 48 to SEQ ID NO: 50. That is, N01 to N03 in FIG. 3 correspond to SEQ ID NO: 48 to SEQ ID NO: 50, respectively. FIG. 4 shows, in order from top to bottom, SEQ ID NO: 51 to SEQ ID NO: 53. That is, A01 to A03 in FIG. 4 correspond to SEQ ID NO: 51 to SEQ ID NO: 53, respectively.

(I-i) Search for Non-Natural Disulfide Bond Introduction Sites

A structure search was performed using computational chemistry software "MOE" of Chemical Computing Group. Among the conformational data of human Fab in Protein Data Bank (PDB), the data of PDB ID: 1L7I, where the heavy chain is of γ1 type and the light chain is of κ type and the resolution of 1.8 Å was the highest was used for the initial structure of IgG1 antibody wherein the light chain is of κ type; and the data of PDB ID: 2FB4, where the heavy chain is of γ1 type and the light chain is of λ type, and the resolution of 1.9 Å was the highest was used for the initial structure of IgG1 antibody wherein the light chain is of λ type.

When introducing a new disulfide bond, in view of the report that it is important for the distance between the a carbons and the distance between the β carbons of the residues of the mutation origin to be rather close (Sowdhamini R. et al., *Protein Eng.*, 95-103, 1989), a search was made for residue pairs with a distance between a carbons to be 7.0 Å or less and a distance between β carbons to be 5.5

Å or less for κ chain, and residue pairs with a distance between a carbons to be 10 Å or less and a distance between β carbons to be 8 Å or less for λ chain.

(I-ii) Obtainment of Human Light Chain Genes

A human κ type light chain gene was obtained by PCR cloning using a cDNA library prepared from RNA derived from the peripheral blood leukocytes of a healthy individual (adult) (BioChain, C1234148-10) as the template. The PCR primers for the process were designed in reference to GenBank entry: J00241 (sequences P01 and P02 in FIG. 2). Additionally, to make cloning easy, the two primers were made to include a restriction enzyme site in advance. After cloning the PCR products into a cloning vector (pBluescriptII, etc.), the base sequences were verified, and the clone with the sequence between the two recognition sequences identical to J00241 was selected (wild-type: sequence N01 in FIG. 3, sequence A01 in FIG. 4). A gene of a light chain variable region (anti-CD20 antibody, anti-CD37 antibody or anti-DR5 antibody) comprising a secretory signal sequence linked to an upstream part of the above sequence (consistent with the sequence of an anti-DR5 antibody) was cloned, and this and an already-cloned κ chain constant region were arranged in this order downstream of a promoter in an expression vector.

A human λ type light chain gene was obtained using the same process as the human κ type light chain. The PCR primers for the process were designed in reference to GenBank entry: J00252 (sequence P03 and P04 in FIG. 2). Moreover, to make cloning easy, the two primers were made to include a restriction enzyme site in advance. After cloning the PCR products into a cloning vector (pBluescriptII, etc.), the base sequences were verified, and the clone with the sequence between the two recognition sequences identical to J00252 was selected. Using the vector into which this λ chain constant region was cloned as a template, a sense primer designed to connect a light chain variable region and the λ chain constant region (sequence P05 in FIG. 2) and an antisense primer of the λ chain constant region C-terminus (sequence P04 in FIG. 2) were used to perform PCR again, and a λ chain constant region for connecting a variable region (wild-type: sequence N02 in FIG. 3, sequence A02 in FIG. 4) was obtained. A gene of a light chain variable region (anti-CD20 antibody) comprising a secretory signal sequence linked to an upstream part of the above sequence (consistent with the sequence of an anti-DR5 antibody) was cloned, and this and the λ chain constant region for connecting a variable region were arranged in this order downstream of a promoter in an expression vector.

(I-iii) Obtainment of Human IgG1 Genes

Genes of human IgG1 heavy chain constant regions (CH1 region to CH3 region) were obtained by PCR cloning after synthesizing cDNA using RNA extracted from the peripheral blood leukocytes of a healthy individual (adult) as the material. The PCR primers for the process were designed in reference to GenBank entry: J00228 (sequences P06 and P07 in FIG. 2). Moreover, to make cloning easy, the two PCR primers were made to include a restriction enzyme site in advance. After cloning the PCR products into a cloning vector (pBluescriptII, etc.), the base sequences were verified, and the clone with the sequence between the two recognition sequences identical to J00228 was selected (wild-type: sequence N03 in FIG. 3, sequence A03 in FIG. 4). A gene of a heavy chain variable region (anti-CD20 antibody, anti-CD37 antibody or anti-DR5 antibody) comprising a secretory signal sequence linked to an upstream part of the above sequence was cloned, and this and an already-cloned heavy chain constant region were arranged in this order downstream of a promoter in an expression vector.

(I-iv) Obtainment of Non-Natural Disulfide Bond Antibody Expression Vectors

In order to disable a light chain-heavy chain natural disulfide bond, the Cys were substituted with Ser (light chain: C214S, heavy chain: C220S) in parallel.

For the κ type light chain, a sense primer (sequence P08 in FIG. 2) having the C214S mutation and an antisense primer (sequence P09 in FIG. 2) were designed, and by using various primers (sequences P10-P18 in FIG. 2) for mutating Cys designed upstream thereof, a sense primer (sequence P19 in FIG. 2) derived from a vector sequence designed most upstream and an antisense primer (sequence P20 in FIG. 2) derived from a vector sequence designed most downstream in an appropriate combination, PCR was performed with a human κ type light chain gene (wild-type) as the template, and gene fragment groups with the desired mutation were obtained. After appropriately connecting them by PCR and cloning, the sequences (sequences N04-N08 in FIG. 3, A04-A08 in FIG. 4) were verified. Then each replaced a homologous region of the wild-type gene on an expression vector, and the desired mutated light chain gene groups were obtained.

For the λ type light chain, an antisense primer (sequence P21 in FIG. 2) having the C214S mutation was designed, and by using various primers (sequence P22-P26 in FIG. 2) for mutating Cys designed upstream thereof and a sense primer (sequence P05 in FIG. 2) designed most upstream in an appropriate combination, PCR was performed with a human λ type light chain gene (wild-type) as the template, and gene fragment groups with the desired mutation were obtained. After appropriately connecting them by PCR and cloning, the sequences (sequence N09-N11 in FIG. 3 and sequences A09-A11 in FIG. 4) were verified. Then each replaced a homologous region of the wild-type gene on an expression vector, and the desired mutated light chain gene groups were obtained.

For the heavy chain, a sense primer (sequence P27 in FIG. 2) having the C220S mutation, an antisense primer (sequence P28 in FIG. 2), various primers (sequences P29-P43 in FIG. 2) for mutating Cys, a sense primer derived from a heavy chain variable region of an anti-CD20 antibody designed most upstream, and an antisense primer (sequence P44 in FIG. 2) derived from a CH2 domain designed most downstream were used to perform PCR with a human IgG1 gene as the template, and gene fragment groups with the desired mutation were obtained. After appropriately performing PCR to connect them as necessary and cloning, the sequences (sequences N12-N19 and A12-A19 in FIG. 3 and FIG. 4) were verified. Then each replaced a homologous region of the wild-type gene on an expression vector, and the desired mutated heavy chain gene groups were obtained.

(I-v) Obtainment of Protein a Affinity Defective Antibody Expression Vectors

When preparing a bispecific antibody, one of the heavy chains was designed to be defective in its protein A binding capacity so as to be able to easily and efficiently purify a molecule (heteromer) wherein heavy chains of different sequences are bound using a difference in protein A binding capacity as an indicator. That is, the residues on IgG1, i.e., H435 and Y436, were substituted with IgG3 type residues which do not have protein A binding capacity (H435R/Y436F). It has been verified already that a heteromer ([1]/[3]) consisting of a wild-type heavy chain (shown as [1]) and the mutated heavy chain (shown as [3]) exhibits an intermediate protein A binding capacity between a wild-type homomer ([1]/[1]) and a mutant homomer ([3]/[3]), and that as a result thereof, the three can be discretely purified by affinity chromatography using a protein A column.

A sense primer (sequence P45 in FIG. 2) having the H435R/Y436F mutations and an antisense primer (sequence P46 in FIG. 2) were designed for a human IgG3 type heavy chain in reference to GenBank entry: X03604. These and a sense primer (sequence P19 in FIG. 2) and an antisense primer (sequence P47 in FIG. 2) derived from a vector sequence were used to perform PCR with a human IgG1 heavy chain constant region gene as the template, and a gene fragment upstream of the mutations and a gene fragment downstream of the mutations were obtained. The two fragments were connected by PCR. Further, with this as the template, upstream and downstream primers (sequences P19, P47 in FIG. 2) were used to perform PCR to obtain the desired gene fragment. Then cloning was performed, and the sequence (sequence N20 in FIG. 3, sequence A20 in FIG. 4) was verified. Next, after a restriction enzyme treatment to prepare a SacII-XhoI fragment, this replaced a homologous region of the wild-type gene on an expression vector, and a vector expressing the desired mutated heavy chain gene was obtained.

[Expression and Purification of Various Antibodies]

(II-i) Gene Transfer

After using a commercially available kit to purify various expression vectors at gene transfer quality, 293fectin (Invitrogen, 12347-019) was used for gene transfer into FreeStyle 293-F cells (Invitrogen, R790-07) according to the manufacturer's instructions.

(II-ii) Purification by Affinity Chromatography

When purifying a parent antibody (each antibody forming the basis for the multispecific antibodies) or the like from a culture supernatant, HiTrap Protein-A HP column or HiTrap Protein-G HP column (GE Healthcare Biosciences) was used to perform bulk purification according to the manufacturer's instructions. The obtained purification fraction was dialyzed against PBS-T (10 mM $Na_2HPO_4$, 150 mM NaCl, 0.07% Tween-80, pH 7.0), and stored at 4° C. until use.

(II-iii) Bispecific Antibody Purification by Strong Cation Exchange Chromatography A strong cation exchange column PL-SCX (Polymer Laboratories, 4.6φ×150 mm, 1000 Å) was used. With a mobile phase solution A (10 mM MES, pH 6.0), a mobile phase solution B (500 mM NaCl, 10 mM MES, pH 6.0) and a flow rate of 1 mL/min, an initial mobile phase with a mixing rate of mobile phase solution B at 2% was delivered at five times or more column volume equivalents to equilibrate the column in advance. 0.2-1 mg of a weakly binding fraction (heavy chain [1] [3] type heteromer=bispecific antibody) purified by protein A affinity chromatography was loaded (0 min) and allowed to bind electrostatically to the column. After washing for 5 minutes with the above initial mobile phase (0→5 min), it was run for 47.5 minutes at a linear gradient with the mixing rate of solution B increasing at 0.8%/min (5→52.5 min, 2→40%), and the bound components were collected sequentially. Then the mixing rate of solution was made 100% immediately, and the column was washed. During this period, absorption at 280 nm was recorded, and the elution behavior of proteins was monitored. The recovered bispecific antibody (main peak) was dialyzed against PBS-T (pH 7.0) as necessary, and stored at 4° C.

[Characteristics Analysis of Antibodies]

(III-i) SDS-PAGE

To verify that the purified bispecific antibody has the molecular weight as designed, SDS-PAGE was performed under non-reducing conditions in the following process. Moreover, the state of light chain-heavy chain bond restriction was also verified from the results.

After allowing each sample to form an SDS complex using a sample treatment solution (manufactured by Cosmo Bio, 423420: Tris-SDS sample treatment solution, etc.), phoresis was performed using a precast gel (manufactured by Marisoru, GM-1020-3N: Nagaiki 10-20%, etc.) of an appropriate acrylamide concentration in the presence of SDS and under non-reducing conditions. Next, the gel was stained using a commonly used staining method, for example, using Coomassie Brilliant Blue R250 solution, to visualize the protein bands.

(III-ii) F(Ab')$_2$ Analysis

Since a bispecific antibody simultaneously has two types of Fabs derived from two parent antibodies, when F(ab')$_2$ is prepared therefrom, it has the physicochemical characteristic of exhibiting an intermediate property between those from the two parent antibodies. To verify that structurally it truly is bispecific, pepsin treatment and F(ab')2 analysis were performed using the purified bispecific antibody in the following process.

After dissolving 50 μg of the purified bispecific antibody (without dialysis treatment) in 30 mM sodium acetate containing 0.07% Tween (pH 4.0) to obtain a final concentration of about 10 μg/100 μL, immobilized pepsin swollen with 0.2 M sodium acetate (pH 4.0) (Sigma, Pepsin-Agarose from porcine gastric mucosa, etc.) was added at 8.5 U per 50 μg of substrate. After shaking this at 120 rpm for 1 hour at 37° C. to allow the cleavage reaction to occur, it was treated with a centrifugation type filter (manufactured by Takarashuzo, 9040: SUPREC-01, etc.), and the filtrate was collected. Immediately afterwards, 30% by volume of 2.5 M Tris-HCl (pH 8.0) was added and stirred to neutralize the reaction solution. Next, using a buffer with 0.07% of Tween-80 added to mobile phase solution A for HPLC using a strong cation exchange column PL-SCX, dialysis or desalting column treatment was performed. Then analysis by strong cation exchange chromatography was performed according to the above section (II-iii).

(III-iii) Fab Analysis

Since a bispecific antibody simultaneously has two types of Fabs derived from two parent antibodies, when Fab is prepared therefrom, it has the physicochemical characteristic of the two types of Fabs derived from the two parent antibodies being detected. To verify that structurally it truly is bispecific, a papain treatment and Fab analysis were performed using the purified bispecific antibody in the following process.

After dissolving 60 μg of the purified bispecific antibody in 200 μL of PBS-T (pH 7.0), immobilized papain swollen (Sigma, P-4406: Papain-Agarose from papaya latex, etc.) with 30 μL of 1 M Tris-40 mM EDTA (pH 7.4), 30 μL of 10 mM cysteine and 0.1 M Tris-4 mM EDTA (pH 7.4) was added at 0.12 U per 60 μg of substrate. After diluting this to 300 μL with PBS-T (pH 7.0), it was shaken at 120 rpm for 16 hours at 37° C. to allow the cleavage reaction to occur. Next, similar to the above section (III-ii), the mixture was treated with a centrifugation type filter, and the filtrate was collected. Then a buffer exchange was performed by dialysis or desalting column treatment, and analysis by strong cation exchange chromatography was performed according to the above section (II-iii).

(III-iv) Antigen Binding Capacity Analysis

Since a bispecific antibody simultaneously has two types of Fabs derived from two parent antibodies, it has the biological characteristic of being capable of binding to both target cells expressing the corresponding antigens. To verify that structurally it truly is bispecific, a binding capacity analysis was performed using the purified bispecific antibody in the following process.

After seeding target cells in a 96-well dish at 2×10⁵ cells/well, 50 μL of the bispecific antibody sample of each concentration dissolved in 5% FBS-containing PBS (5% FBS/PBS) was added, and the cells were dispersed. After allowing to react for 30 minutes on ice, the cells were washed twice with 200 μL of 5% FBS/PBS. Next, 50 μL of a phycoerythrin (PE)-tagged anti-human IgG Fc antibody (for example, Rockland, 709-1817, 100-fold dilution) diluted with 5% FBS/PBS was added, and again the cells were dispersed. After allowing to react for 30 minutes on ice, they were washed twice as before. Lastly, after dispersing them in 200 μL of 1% formalin, the fluorescence level exhibited by each target cell was measured by a flow cytometer, and the mean fluorescence intensity (MFI) was calculated.

[Selection of Mutant Candidates with an Introduced Non-Natural Disulfide Bond]

After searching by computational chemistry software "MOE", excluding one set with a high possibility of forming a disulfide bond with an existing Cys residue present in the wild-type antibody in the κ chain, nine sets of residue pair candidates into which a non-natural disulfide bond can be introduced were found. Their positions, distances between a carbons (Cα-Cα') and distances between β carbons (Cβ-Cβ') are shown in Table 3. Additionally, in the λ chain, five sets of residue pair candidates into which a non-natural disulfide bond can be introduced were found. Their positions, distances between a carbons (Cα-Cα') and distances between β carbons (Cβ-Cβ') are shown in Table 4. Moreover, the numbering of the amino acid residues where the light chain is a λ chain was determined by a sequence comparison with the κ chain.

Summary of search results for sites to introduce a non-natural disulfide bond

TABLE 3

| Cys1m | Position (light chain) | Position (heavy chain) | Cα-Cα' (Å) | Cβ-Cβ' (Å) |
|---|---|---|---|---|
| (a) | F116C | S134C | 4.37 | 4.04 |
| (b) | " | A141C | 6.94 | 4.16 |
| (c) | F118C | L128C | 5.76 | 4.35 |
| (d) | S121C | F126C | 6.59 | 4.54 |
| (e) | " | P127C | 6.46 | 5.20 |
| (f) | Q124C | F126C | 6.53 | 4.66 |
| (g) | S162C | F170C | 6.30 | 4.07 |
| (h) | " | P171C | 6.22 | 5.02 |
| (i) | " | V173C | 6.77 | 5.35 |

TABLE 4

| Cys1m | Position (light chain: λ chain) | Position (heavy chain) | Cα-Cα' (Å) | Cβ-Cβ' (Å) |
|---|---|---|---|---|
| (j) | F118C | L128C | 6.47 | 4.43 |
| (k) | E124C | F126C | 6.72 | 4.76 |
| (l) | T162C | F170C | 9.94 | 7.58 |
| (m) | " | P171C | 8.12 | 6.03 |
| (n) | " | V173C | 5.66 | 5.10 |

Each mutant shown in Table 3 was actually expressed and verified as to the formation of a light chain-heavy chain non-natural disulfide bond. After individually introducing each mutation of Cys1m (a)-(i) shown in Table 3 into the wild-type anti-CD20 antibody gene and wild-type anti-CD37 antibody gene on the expression vectors, each was gene transferred/expressed in FreeStyle 293-F cells, and antibody components were quickly purified from culture supernatants thereof by HiTrap protein A column. The results of subjecting them to SDS-PAGE are shown in FIG. 5 and FIG. 6. Other than Cys1m (e), the mutants were observed to exhibit a main band in a location of about 150 kDa which is a molecular weight equal to that of the wild-type.

Moreover, each mutant shown in Table 4 was also actually expressed and verified as to the formation of a light chain-heavy chain non-natural disulfide bond. A λ1 type CL gene was grafted into the gene of the CL region of the wild-type anti-CD20 antibody on the expression vector to form a λ1 type CL gene expression vector. After individually introducing each mutation of Cys1m (j)-(n) shown in Table 4 into this λ1 type CL gene expression vector, each was gene transferred/expressed in FreeStyle293-F cells as above, and antibody components were quickly purified from culture supernatants thereof by HiTrap protein A column. The results of subjecting them to SDS-PAGE are shown in FIG. 7. The mutants were all observed to exhibit a main band in a location of about 150 kDa which is a molecular weight equal to that of the wild-type. Therefore, it was verified that the introduction of a Cys1m mutation can form a light chain-heavy chain non-natural disulfide bond, and is applicable independently of the light chain subtype of the antibody.

On the other hand, after introducing the Cys1m (f) mutation shown in Table 3 into the wild-type anti-HER2 antibody gene, anti-EGFR antibody gene and anti-CD52 antibody gene on the expression vectors, they were gene transferred/expressed into FreeStyle293-F cells as above, and antibody components were quickly purified from culture supernatants thereof and subjected to SDS-PAGE. The results are shown in FIG. 8. The antibodies with the Cys1m (f) type mutation were all observed to exhibit a main band in a location of about 150 kDa which is a molecular weight equal to that of the wild-type, and it was verified that the introduction of a Cys1m mutation is applicable independently of the sequence of a variable region of an antibody.

Next, each light chain or heavy chain mutant was verified as to the formation of a disulfide bond with a natural light chain or heavy chain. The above mutation was introduced into one of the light chain gene or heavy chain gene of the wild-type anti-CD20 antibody on the expression vector, and they were used in an expression experiment and an SDS-PAGE analysis for the verification thereof as above. The SDS-PAGE results when a mutation was introduced into the light chain are shown in FIG. 9 and FIG. 10. In the light chain mutants other than κ chain S121C (used in Cys1m (d) and (e)) and λ chain E124C (used in Cys1m (k)), a band was observed in locations thought to be a heavy chain dimer and the light chain, and no band was seen in the location of about 150 kDa which is the molecular weight equivalent to that of the wild-type. On the other hand, the SDS-PAGE results when a mutation was introduced into the heavy chain are shown in FIG. 10 and FIG. 11. In heavy chain mutants other than heavy chain S134C (used in Cys1m (a)), a band was observed in locations thought to be a light chain monomer as well as a heavy chain dimer and monomer, and no band was seen in the location of about 150 KDa which is the molecular weight equivalent to that of the wild-type. Therefore, it was clear that each light chain or heavy chain mutant does not form a disulfide bond with a natural light chain or heavy chain.

Lastly, whether or not a non-natural disulfide bond introduced in the constant region affected antigen binding capacity was verified. The results of using Cys1m type anti-CD20 antibodies quickly purified by HiTrap protein A column to examine antigen binding capacity against CD20 antigen-expressing Ramos cells are shown in FIG. 12-FIG. 16. There appeared to be almost no difference between the antigen binding capacities of Cys1m (a)-(n) mutants and that of the wild-type antibody (wt).

Additionally, for the anti-CD37 antibodies having a non-natural disulfide bond (Cys1m type anti-CD37 antibodies), CD37 antigen-expressing Ramos cells were used to examine the antigen binding capacities of Cys1m (a)-(i) mutants in the same manner as the experiment for the anti-CD20 antibodies, and results similar to those of the anti-CD20 antibodies were obtained (FIGS. 17-19).

Colligating the above results, the cysteine residues forming a non-natural disulfide bond in the above experiments had few crosses with a natural disulfide bond, and had a high binding selectivity. Moreover, the introduced non-natural disulfide bond did not affect the antigen binding capacity.

[Preparation of Bispecific Antibodies]

As the combination partner of the anti-CD20 antibody (αCD20) having a non-natural disulfide bond used in the expression experiments, an anti-DR5 antibody (αDR5) or an anti-CD37 antibody (αCD37) were used to prepare bispecific antibodies. The Cys1m used in the examples are the five types of (b), (c), (f), (g) and (h), and they were introduced into αCD20. A protein A affinity defect mutation for purifying a heavy chain heteromer ([1][3] conjugate) was introduced into αDR5, αCD37 or αCD20 (indicated as [3]).

The protein A affinity chromatography results when preparing bispecific antibodies αCD20 (Cys1m)/αDR5 are shown in FIG. 20. The initial large peak observed during washing immediately after loading is a heavy chain [3][3] type homomer (corresponding to αDR5) that could not bind to protein A. By the elution operation afterwards, a weakly binding heavy chain [1][3] type heteromer (corresponding to αCD20 (Cys1m)/αDR5, bispecific antibody) around 35-40 minutes and subsequently a strongly binding heavy chain [1][1] type homomer (corresponding to αCD20) around 55-60 minutes were recovered. The mutants with a non-natural disulfide bond all had the same elution profile as the wild-type (wt), and the mutations did not have a bad effect on the purification method. Even in the case of αDR5/αCD20 (Cys1m) where a protein A affinity defect mutation [3] was introduced into αCD20 in the same combination, three peaks were similarly detected (data unpublished).

When similar experiments were performed on the other combination, the bispecific antibody αCD20 (Cys1m)/αCD37 combination, three peaks were similarly detected, and from the one eluted earliest, they corresponded to αCD37 (heavy chain [3][3] type homomer), αCD20 (Cys1m)/αCD37 (heavy chain [1][3] type heteromer), αCD20 (heavy chain [1][1] type homomer).

The heavy chain [1][3] type heteromer (bispecific antibody) fraction was collected in each case, subjected to a buffer exchange, and then subjected to strong cation exchange chromatography, and the main peak thereof was collected. Again a buffer exchange was performed, and a final purified product of the bispecific antibody was obtained.

[Quality Verification of Bispecific Antibodies]

A bispecific antibody capable of simultaneously binding to two different types of antigens has simultaneously Fabs derived from two types of parent antibodies that can recognize respective antigens. Therefore, in a F(ab')$_2$ analysis thereof, theoretically, one peak will be detected at an elution time between those of F(ab')$_2$ prepared from the two parent antibodies. The purified bispecific antibodies αCD20 (Cys1m)/αDR5 were treated with the enzyme pepsin, and the F(ab')$_2$ analysis results are shown in FIG. 21. In the present samples, a main peak was observed around 33 minutes, and this corresponds to the F(ab')$_2$ of the bispecific antibodies. Its elution time is between those of the parent antibodies αDR5 (30 min) and αCD20 (36 min) separately analyzed and shown in FIG. 22.

The results in the case of the other combination, the bispecific antibodies αCD20 (Cys1m)/αCD37, are shown in FIG. 23. For this combination, the F(ab')$_2$ peak was seen after 30 minutes. Similar to the above, this combination also showed an elution time between those of the parent antibodies αCD37 (25 min) and αCD20 (36 min) (FIG. 24).

A bispecific antibody capable of simultaneously binding to two different types of antigens has simultaneously Fabs derived from two types of parent antibodies that recognize respective antigens. Therefore, in a Fab analysis thereof, two peaks will be detected respectively at the same elution time as the Fabs prepared from the two parent antibodies. The purified bispecific antibodies αCD20 (Cys1m)/αDR5 were treated with papain, and the Fab analysis results are shown in FIG. 25. The peak around 18 minutes common to each sample is Fc resulting from the papain cleavage. On the other hand, the peak around 25.5 minutes is αDR5 specific, and the peak at 29-30 minutes is αCD20 specific Fab (FIG. 26). Based on the analysis results of separately prepared antibody samples wherein the light chain was forced to bind erroneously, the Fabs of the light chain mispairings in the combination elute around 22 minutes in the case of αDR5 (light chain)-αCD20 (heavy chain) and, on the other hand, around 37 minutes in the case of αCD20 (light chain)-αDR5 (heavy chain) (FIG. 26). Peaks derived from impurities such as these mispaired Fabs were not detected at all in the three present purified samples.

The Fab analysis results of the bispecific antibodies αCD20 (Cys1m)/αCD37 are shown in FIG. 27. Additionally, the analysis results for each parent antibodies are shown in FIG. 27. The bispecific antibody samples all had results similar to the above. That is, a Fc peak around 18 minutes, an αCD37 Fab peak around 23 minutes, and an αCD20 Fab peak at 29-30 minutes were detected. The analysis results of forcedly mispaired antibodies that were prepared separately showed that the Fabs of the light chain mispairings in the combination elute around 22.5 minutes in the case of αCD37 (light chain)-αCD20 (heavy chain), and on the other hand, around 28 minutes and around 31 minutes in the case of αCD20 (light chain)-αCD37 (heavy chain) (FIG. 28). Peaks derived from impurities such as these mispaired Fabs were not detected at all in the three present purified samples.

In order to be able to directly show the effect of light chain-heavy chain pairing restriction by the introduction of a non-natural disulfide bond, it is demonstrated by Fab analysis using protein A affinity purified samples. The results of bispecific antibodies αCD20 (Cys1m)/αDR5 are shown in FIG. 29, and the results of αCD20 (Cys1m)/αCD37 are shown in FIG. 30. In the cases of wild-types without a mutation, the respective two types of mispaired Fabs were prominently detected in all combination examples. On the other hand, they were reduced considerably when a mutation was introduced, and particularly in the cases of Cys1m (f) and (g), they were at slightly detected levels.

FIGS. 31 and 32 show that the bispecific antibodies αCD20 (Cys1m)/αCD37 are functional bispecific antibodies. In a situation where the negative control, i.e., parent antibody αCD37 (wt), cannot bind, αCD20 (Cys1m)/αCD37 clearly had binding capacity towards CD20 positive CD37 negative cells (SP2/0 cells into which αCD20 gene was introduced and its expression confirmed by FACS). Even towards the other test cells, i.e., CD20 negative CD37 positive cells (SP2/0 cells into which a CD37 gene was introduced and its expression confirmed by FACS), in a situation where the negative control, i.e. the parent antibody αCD20 (wt), cannot bind, αCD20 (Cys1m)/αCD37 had binding capacity. Similarly, the result of being functionally bispecific was also obtained for bispecific antibodies αDR5/αCD20 (Cys1m) (FIGS. 33 and 34), showing that the utility of the technique is universal.

Based on the results shown above, it was verified that the technique of restricting an inter-chain bond using a non-natural disulfide bond of the present invention, an antibody having different Fab regions, such as a bispecific antibody, can be efficiently and easily made.

The various embodiments explained in the description of modes for carrying out the invention above do not restrict the present invention, and are disclosed with the intention of exemplification. The technical scope of the present invention is defined by the recitations of the claims, and those skilled in the art can make various changes in design within the technical scope of the invention recited in the claims.

Furthermore, the disclosures of the patents, patent applications and publications cited in the present specification are all incorporated in the present specification by reference.

The invention claimed is:

1. A method for making an antibody comprising a first Fab region which comprises a first light chain and heavy chain, and a second Fab region which comprises a second light chain and heavy chain each being different from said first light chain and heavy chain; the method comprising:
   a) substituting at least one amino acid residue other than cysteine in a CL region and a CH1 region in the first Fab region of a parent antibody of said antibody with a cysteine residue which forms a disulfide bond, and
   b) forming a non-natural disulfide bond in the first Fab region by said cysteine residue which forms a disulfide bond,
   wherein due to the presence of said non-natural disulfide bond, the first Fab region forms a disulfide bond at a position different from the second Fab region,
   wherein the non-natural disulfide bond is formed by cysteine residues introduced in at least one set of light chain-heavy chain positions selected from light chain position 124-heavy chain position 126, and light chain position 162-heavy chain position 170, and
   wherein the light chain-heavy chain positions are numbered based on Kabat EU numbering system.

2. The method according to claim 1, wherein the antibody is a bispecific antibody.

3. The method according to claim 1, wherein the antibody is one wherein at least two antibody fragments are connected through a linker or directly.

4. The method according to claim 1, wherein the antibody is an antibody fragment.

5. The method according to claim 1, wherein a Fc region of the antibody is substituted with another molecule.

6. The method according to claim 1, wherein the antibody is a chimeric antibody, a humanized antibody or a human antibody.

7. The method according to claim 1, wherein a natural disulfide bond is not formed between a CL region and a CH1 region of at least one Fab region.

8. The method according to claim 1, wherein the position of a disulfide bond between a CL region and a CH1 region in one Fab region is entirely different from the position of a disulfide bond between a CL region and a CH1 region in at least one other Fab region.

9. An antibody comprising at least two different Fab regions,
   wherein at least one Fab region comprises a cysteine residue which forms a non-natural disulfide bond between a CL region and a CH1 region, thereby forming a non-natural disulfide bond,
   wherein due to the presence of said non-natural disulfide bond, the position of a disulfide bond between a CL region and a CH1 region in a Fab region is different from the position of a disulfide bond between a CL region and a CH1 region in at least one other Fab region,
   wherein the non-natural disulfide bond is formed by cysteine residues introduced in at least one set of light chain-heavy chain positions selected from light chain position 124-heavy chain position 126, and light chain position 162-heavy chain position 170, and
   wherein the light chain-heavy chain positions are numbered based on Kabat EU numbering system.

10. The antibody according to claim 9, which comprises two different Fab regions.

11. The antibody according to claim 9, wherein the antibody is a bispecific antibody.

12. The antibody according to claim 9, wherein the antibody is one wherein at least two antibody fragments are connected through a linker or directly.

13. The antibody according to claim 9, wherein the antibody is an antibody fragment.

14. The antibody according to claim 9, wherein an Fc region of the antibody is substituted with another molecule.

15. The antibody according to claim 9, wherein the antibody is a chimeric antibody, a humanized antibody or a human antibody.

16. The antibody according to claim 9, wherein a natural disulfide bond is not formed between a CL region and a CH1 region of at least one Fab region.

17. The antibody according to claim 9, wherein the position of a disulfide bond between a CL region and a CH1 region in one Fab region is entirely different from the position of a disulfide bond between a CL region and a CH1 region in at least one other Fab region.

18. The antibody according to claim 9, which specifically binds to at least CD20.

19. A composition comprising a mixture of at least two antibodies comprising Fab regions, the Fab regions being different between the at least two antibodies,
   wherein at least one Fab region comprises a cysteine residue which forms a non-natural disulfide bond between a light chain and a heavy chain, thereby forming a non-natural disulfide bond,
   wherein due to the presence of said non-natural disulfide bond, the position of a disulfide bond between a light chain and a heavy chain of a Fab region is different from the position of a disulfide bond between a light chain and a heavy chain of at least one other Fab region,
   wherein the non-natural disulfide bond is formed by cysteine residues introduced in at least one set of light chain-heavy chain positions selected from light chain position 124-heavy chain position 126, and light chain position 162-heavy chain position 170, and
   wherein the light chain-heavy chain positions are numbered based on Kabat EU numbering system.

* * * * *

```
                             SEQUENCE LISTING

<160> NUMBER OF SEQ ID NOS: 53

<210> SEQ ID NO 1
<211> LENGTH: 27
<212> TYPE: DNA
<213> ORGANISM: Artificial Sequence
<220> FEATURE:
<223> OTHER INFORMATION: Primer

<400> SEQUENCE: 1
tttcgtacgg tggctgcacc atctgtc                                              27

<210> SEQ ID NO 2
<211> LENGTH: 33
<212> TYPE: DNA
<213> ORGANISM: Artificial Sequence
<220> FEATURE:
<223> OTHER INFORMATION: Primer

<400> SEQUENCE: 2
ttttctagat caacactctc ccctgttgaa gct                                       33

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3
tttaagcttg gtcagcccaa ggc                                                  23

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
cgactctaga ctatgaacat tctgt                                                25

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
```

-continued aaacgtacgg tggccaaccc cactgtcact        30

<210> SEQ ID NO 6
<211> LENGTH: 29
<212> TYPE: DNA
<213> ORGANISM: Artificial Sequence
<220> FEATURE:
<223> OTHER INFORMATION: Primer

<400> SEQUENCE: 6
tttgctagca ccaagggccc atcggtctt        29

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
aaactcgagt catttacccg gagacaggga        30

<210> SEQ ID NO 8
<211> LENGTH: 30
<212> TYPE: DNA
<213> ORGANISM: Artificial Sequence
<220> FEATURE:
<223> OTHER INFORMATION: Primer

<400> SEQUENCE: 8
tcaacagggg agagtcctga tctagagtcg        30

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9
cgactctaga tcaggactct cccctgttga        30

<210> SEQ ID NO 10
<211> LENGTH: 44
<212> TYPE: DNA
<213> ORGANISM: Artificial Sequence
<220> FEATURE:
<223> OTHER INFORMATION: Primer

<400> SEQUENCE: 10
aaacgtacgg tggctgcacc atctgtctgc atcttcccgc catc        44

<210> SEQ ID NO 11
<211> LENGTH: 30
<212> TYPE: DNA
<213> ORGANISM: Artificial Sequence
<220> FEATURE:
<223> OTHER INFORMATION: Primer

<400> SEQUENCE: 11
catctgtctt catctgcccg ccatctgatg        30

<210> SEQ ID NO 12
<211> LENGTH: 30
<212> TYPE: DNA
<213> ORGANISM: Artificial Sequence

```
<220> FEATURE:
<223> OTHER INFORMATION: Primer

<400> SEQUENCE: 12
catcagatgg cgggcagatg aagacagatg                                    30

<210> SEQ ID NO 13
<211> LENGTH: 30
<212> TYPE: DNA
<213> ORGANISM: Artificial Sequence
<220> FEATURE:
<223> OTHER INFORMATION: Primer

<400> SEQUENCE: 13
ttcatcttcc cgccatgcga tgagcagttg                                    30

<210> SEQ ID NO 14
<211> LENGTH: 30
<212> TYPE: DNA
<213> ORGANISM: Artificial Sequence
<220> FEATURE:
<223> OTHER INFORMATION: Primer

<400> SEQUENCE: 14
caactgctca tcgcatggcg ggaagatgaa                                    30

<210> SEQ ID NO 15
<211> LENGTH: 27
<212> TYPE: DNA
<213> ORGANISM: Artificial Sequence
<220> FEATURE:
<223> OTHER INFORMATION: Primer

<400> SEQUENCE: 15
gatgagtgct tgaaatctgg aactgcc                                       27

<210> SEQ ID NO 16
<211> LENGTH: 27
<212> TYPE: DNA
<213> ORGANISM: Artificial Sequence
<220> FEATURE:
<223> OTHER INFORMATION: Primer

<400> SEQUENCE: 16
tttcaagcac tcatcagatg gcgggaa                                       27

<210> SEQ ID NO 17
<211> LENGTH: 30
<212> TYPE: DNA
<213> ORGANISM: Artificial Sequence
<220> FEATURE:
<223> OTHER INFORMATION: Primer

<400> SEQUENCE: 17
ctcccaggag tgcgtcacag agcaggacag                                    30

<210> SEQ ID NO 18
<211> LENGTH: 30
<212> TYPE: DNA
<213> ORGANISM: Artificial Sequence
<220> FEATURE:
<223> OTHER INFORMATION: Primer

<400> SEQUENCE: 18
ctgtcctgct ctgtgacgca ctcctgggag                                    30
```

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
aattaaccct cactaaaggg                                               20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
gtgccacctg acgtctagat                                               20

<210> SEQ ID NO 21
<211> LENGTH: 32
<212> TYPE: DNA
<213> ORGANISM: Artificial Sequence
<220> FEATURE:
<223> OTHER INFORMATION: Primer

<400> SEQUENCE: 21
ccctctagac tatgaggatt ctgtaggggc ca                                 32

<210> SEQ ID NO 22
<211> LENGTH: 51
<212> TYPE: DNA
<213> ORGANISM: Artificial Sequence
<220> FEATURE:
<223> OTHER INFORMATION: Primer

<400> SEQUENCE: 22
aaacgtacgg tggccaaccc cactgtcact ctgtgcccgc cctcctctga g            51

<210> SEQ ID NO 23
<211> LENGTH: 30
<212> TYPE: DNA
<213> ORGANISM: Artificial Sequence
<220> FEATURE:
<223> OTHER INFORMATION: Primer

<400> SEQUENCE: 23
cctctgagtg cctccaagcc aacaaggcca                                    30

<210> SEQ ID NO 24
<211> LENGTH: 30
<212> TYPE: DNA
<213> ORGANISM: Artificial Sequence
<220> FEATURE:
<223> OTHER INFORMATION: Primer

<400> SEQUENCE: 24
tggaggcact cagaggaggg cgggaacaga                                    30

<210> SEQ ID NO 25
<211> LENGTH: 30
<212> TYPE: DNA
<213> ORGANISM: Artificial Sequence
<220> FEATURE:
<223> OTHER INFORMATION: Primer

<400> SEQUENCE: 25
ggagacctgc aaaccctcca aacagagcaa                              30

<210> SEQ ID NO 26
<211> LENGTH: 30
<212> TYPE: DNA
<213> ORGANISM: Artificial Sequence
<220> FEATURE:
<223> OTHER INFORMATION: Primer

<400> SEQUENCE: 26
ggagggtttg caggtctcca ctcccgcctt                              30

<210> SEQ ID NO 27
<211> LENGTH: 30
<212> TYPE: DNA
<213> ORGANISM: Artificial Sequence
<220> FEATURE:
<223> OTHER INFORMATION: Primer

<400> SEQUENCE: 27
gttgagccca aatcttccga caaaactcac                              30

<210> SEQ ID NO 28
<211> LENGTH: 30
<212> TYPE: DNA
<213> ORGANISM: Artificial Sequence
<220> FEATURE:
<223> OTHER INFORMATION: Primer

<400> SEQUENCE: 28
gtgagttttg tcggaagatt tgggctcaac                              30

<210> SEQ ID NO 29
<211> LENGTH: 44
<212> TYPE: DNA
<213> ORGANISM: Artificial Sequence
<220> FEATURE:
<223> OTHER INFORMATION: Primer

<400> SEQUENCE: 29
tcagctagca ccaagggccc atcggtctgc ccctggcac cctc              44

<210> SEQ ID NO 30
<211> LENGTH: 30
<212> TYPE: DNA
<213> ORGANISM: Artificial Sequence
<220> FEATURE:
<223> OTHER INFORMATION: Primer

<400> SEQUENCE: 30
cccatcggtc ttctgcctgg caccctcctc                              30

<210> SEQ ID NO 31
<211> LENGTH: 30
<212> TYPE: DNA
<213> ORGANISM: Artificial Sequence
<220> FEATURE:
<223> OTHER INFORMATION: Primer

<400> SEQUENCE: 31
gaggagggtg ccaggcagaa gaccgatggg                              30

<210> SEQ ID NO 32

```
<211> LENGTH: 30
<212> TYPE: DNA
<213> ORGANISM: Artificial Sequence
<220> FEATURE:
<223> OTHER INFORMATION: Primer

<400> SEQUENCE: 32
catcggtctt cccctgcgca ccctcctcca                                    30

<210> SEQ ID NO 33
<211> LENGTH: 30
<212> TYPE: DNA
<213> ORGANISM: Artificial Sequence
<220> FEATURE:
<223> OTHER INFORMATION: Primer

<400> SEQUENCE: 33
tggaggaggg tgcgcagggg aagaccgatg                                    30

<210> SEQ ID NO 34
<211> LENGTH: 27
<212> TYPE: DNA
<213> ORGANISM: Artificial Sequence
<220> FEATURE:
<223> OTHER INFORMATION: Primer

<400> SEQUENCE: 34
tccaagtgca cctctggggg cacagcg                                       27

<210> SEQ ID NO 35
<211> LENGTH: 27
<212> TYPE: DNA
<213> ORGANISM: Artificial Sequence
<220> FEATURE:
<223> OTHER INFORMATION: Primer

<400> SEQUENCE: 35
agaggtgcac ttggaggagg gtgccag                                       27

<210> SEQ ID NO 36
<211> LENGTH: 27
<212> TYPE: DNA
<213> ORGANISM: Artificial Sequence
<220> FEATURE:
<223> OTHER INFORMATION: Primer

<400> SEQUENCE: 36
acagcgtgcc tgggctgcct ggtcaag                                       27

<210> SEQ ID NO 37
<211> LENGTH: 27
<212> TYPE: DNA
<213> ORGANISM: Artificial Sequence
<220> FEATURE:
<223> OTHER INFORMATION: Primer

<400> SEQUENCE: 37
gcccaggcac gctgtgcccc cagaggt                                       27

<210> SEQ ID NO 38
<211> LENGTH: 27
<212> TYPE: DNA
<213> ORGANISM: Artificial Sequence
<220> FEATURE:
<223> OTHER INFORMATION: Primer

<400> SEQUENCE: 38
```
gcgtgcacac ctgcccggct gtcctac                                        27

<210> SEQ ID NO 39
<211> LENGTH: 27
<212> TYPE: DNA
<213> ORGANISM: Artificial Sequence
<220> FEATURE:
<223> OTHER INFORMATION: Primer

<400> SEQUENCE: 39
gtaggacagc cgggcaggtg tgcacgc                                        27

<210> SEQ ID NO 40
<211> LENGTH: 28
<212> TYPE: DNA
<213> ORGANISM: Artificial Sequence
<220> FEATURE:
<223> OTHER INFORMATION: Primer

<400> SEQUENCE: 40
cgtgcacacc ttctgcgctg tcctacag                                       28

<210> SEQ ID NO 41
<211> LENGTH: 28
<212> TYPE: DNA
<213> ORGANISM: Artificial Sequence
<220> FEATURE:
<223> OTHER INFORMATION: Primer

<400> SEQUENCE: 41
ctgtaggaca gcgcagaagg tgtgcacg                                       28

<210> SEQ ID NO 42
<211> LENGTH: 27
<212> TYPE: DNA
<213> ORGANISM: Artificial Sequence
<220> FEATURE:
<223> OTHER INFORMATION: Primer

<400> SEQUENCE: 42
ccggcttgcc tacagtcctc aggactc                                        27

<210> SEQ ID NO 43
<211> LENGTH: 27
<212> TYPE: DNA
<213> ORGANISM: Artificial Sequence
<220> FEATURE:
<223> OTHER INFORMATION: Primer

<400> SEQUENCE: 43
ctgtaggcaa gccgggaagg tgtgcac                                        27

<210> SEQ ID NO 44
<211> LENGTH: 26
<212> TYPE: DNA
<213> ORGANISM: Artificial Sequence
<220> FEATURE:
<223> OTHER INFORMATION: Primer

<400> SEQUENCE: 44
tgctcctccc gcggctttgt cttggc                                         26

<210> SEQ ID NO 45
<211> LENGTH: 30
<212> TYPE: DNA

<213> ORGANISM: Artificial Sequence
<220> FEATURE:
<223> OTHER INFORMATION: Primer

<400> SEQUENCE: 45
ggctctgcac aaccgcttca cgcagaagag                                           30

<210> SEQ ID NO 46
<211> LENGTH: 30
<212> TYPE: DNA
<213> ORGANISM: Artificial Sequence
<220> FEATURE:
<223> OTHER INFORMATION: Primer

<400> SEQUENCE: 46
ctcttctgcg tgaagcggtt gtgcagagcc                                           30

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
taatacgact cactataggg                                                      20

<210> SEQ ID NO 48
<211> LENGTH: 330
<212> TYPE: DNA
<213> ORGANISM: Homo sapiens

<400> SEQUENCE: 48
cgtacggtgg ctgcaccatc tgtcttcatc ttcccgccat ctgatgagca gttgaaatct          60
ggaactgcct ctgttgtgtg cctgctgaat aacttctatc ccagagaggc caaagtacag         120
tggaaggtgg ataacgccct ccaatcgggt aactcccagg agagtgtcac agagcaggac         180
agcaaggaca gcacctacag cctcagcagc accctgacgc tgagcaaagc agactacgag         240
aaacacaaag tctacgcctg cgaagtcacc catcagggcc tgagctcgcc cgtcacaaag         300
agcttcaaca ggggagagtg ttgatctaga                                          330

<210> SEQ ID NO 49
<211> LENGTH: 324
<212> TYPE: DNA
<213> ORGANISM: Homo sapiens

<400> SEQUENCE: 49
cgtacggtgg ccaaccccac tgtcactctg ttcccgccct cctctgagga gctccaagcc          60
aacaaggcca cactagtgtg tctgatcagt gacttctacc cgggagctgt gacagtggcc         120
tggaaggcag atggcagccc cgtcaaggcg ggagtggaga ccaccaaacc ctccaaacag         180
agcaacaaca agtacgcggc cagcagctac ctgagcctga cgcccgagca gtggaagtcc         240
cacagaagct acagctgcca ggtcacgcat gaagggagca ccgtggagaa gacagtggcc         300
cctacagaat gttcatagtc taga                                                324

<210> SEQ ID NO 50
<211> LENGTH: 999
<212> TYPE: DNA
<213> ORGANISM: Homo sapiens

<400> SEQUENCE: 50

```
gctagcacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagaa agttgagccc   300
aaatcttgtg acaaaactca cacatgccca ccgtgcccag cacctgaact cctgggggga   360
ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacaac   540
agcacgtacc gggtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag ggcagccccg agaaccacag gtgtacaccc tgcccccatc ccgggatgag   720
ctgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctac agcaagctca ccgtggacaa gagcaggtgg   900
cagcagggga acgtcttctc atgctccgtg atgcatgagg ctctgcacaa ccactacacg   960
cagaagagcc tctccctgtc tccgggtaaa tgactcgag                          999
```

<210> SEQ ID NO 51
<211> LENGTH: 107
<212> TYPE: PRT
<213> ORGANISM: Homo sapiens

<400> SEQUENCE: 51

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105

<210> SEQ ID NO 52
<211> LENGTH: 105
<212> TYPE: PRT
<213> ORGANISM: Homo sapiens

<400> SEQUENCE: 52

Arg Thr Val Ala Asn Pro Thr Val Thr Leu Phe Pro Pro Ser Ser Glu
1               5                   10                  15
Glu Leu Gln Ala Asn Lys Ala Thr Leu Val Cys Leu Ile Ser Asp Phe
            20                  25                  30
Tyr Pro Gly Ala Val Thr Val Ala Trp Lys Ala Asp Gly Ser Pro Val

```
                    35                  40                  45
Lys Ala Gly Val Glu Thr Thr Lys Pro Ser Lys Gln Ser Asn Asn Lys
                 50                  55                  60

Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                 85                  90                  95

Lys Thr Val Ala Pro Thr Glu Cys Ser
                100                 105

<210> SEQ ID NO 53
<211> LENGTH: 330
<212> TYPE: PRT
<213> ORGANISM: Homo sapiens

<400> SEQUENCE: 53

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
                 35                  40                  45

Gly Val His Thr Phe Pro Ala Val Leu Gln Ser Ser Gly Leu Tyr Ser
                 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```